(12) United States Patent
Tsuji

(10) Patent No.: US 7,824,860 B2
(45) Date of Patent: Nov. 2, 2010

(54) APPLICATION OF APRATAXIN GENE TO DIAGNOSIS AND TREATMENT FOR EARLY-ONSET SPINOCEREBELLAR ATAXIA (EAOH)

(75) Inventor: Shoji Tsuji, Niigata (JP)

(73) Assignee: Athena Diagnostics, Inc., Worcester, MA (US)

( * ) Notice: Subject to any disclaimer, the term of this patent is extended or adjusted under 35 U.S.C. 154(b) by 352 days.

(21) Appl. No.: 11/496,284

(22) Filed: Jul. 31, 2006

(65) Prior Publication Data

US 2006/0292622 A1 Dec. 28, 2006

Related U.S. Application Data

(62) Division of application No. 10/209,609, filed on Aug. 1, 2002, now Pat. No. 7,119,186.

(30) Foreign Application Priority Data

Sep. 14, 2001 (JP) ............... 2001-279719

(51) Int. Cl.
*C07H 21/04* (2006.01)
*C12Q 1/68* (2006.01)
(52) U.S. Cl. .................. 435/6; 435/91.1; 435/91.2; 536/23.1; 536/24.3
(58) Field of Classification Search .............. None
See application file for complete search history.

(56) References Cited

U.S. PATENT DOCUMENTS

2003/0092019 A1* 5/2003 Meyer et al. ............ 435/6

FOREIGN PATENT DOCUMENTS

WO WO 01/55376 A1 8/2001

OTHER PUBLICATIONS

Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Lucentini (The Scientist; 2004, vol. 24, p. 20).*
Date et al. (Nature Genetics, vol. 29, pp. 184-188, Oct. 2001).*
Moreira et al. (Nature Genetics, vol. 2, pp. 189-193, Oct. 2001).*
NCBI database Accession Nos. BAA90985 (protein) & AK000164 (nucleic acid), GI: 7020073, pp. 1-4, Feb. 22, 2000.
NCBI database Accession Nos. AAH01628 (protein) & BC001628 (nucleic acid), GI: 12804442, pp. 1-4, Jul. 12, 2001.
Database EM—HUM 'Online !, Database Accession No. AK000164, pp. 1-2, XP-002259870, "*Homo sapiens* cDNA FLJ20157 FIS, Clone COL08833", Feb. 22, 2000.
Moreira, M.D.C., et al., American Journal of Human Genetics, 68(2): 501-508, XP-002259869, "Homozygosity Mapping of Portuguese and Japanese Forms of Ataxia-Oculomotor Apraxia to 9p 13, and Evidence for Genetic Heterogeneity", Feb. 2001.

(Continued)

*Primary Examiner*—Jeanine A Goldberg
(74) *Attorney, Agent, or Firm*—Hamilton, Brook, Smith, Reynolds, P.C.

(57) ABSTRACT

The present invention provides polynucleotides and proteins, which are involved in early-onset spinocerebellar ataxia with ocular motor apraxia and hypoalbuminemia (EAOH); and methods of using the polynucleotides and/or proteins to treat and/or diagnose EAOH.

13 Claims, 9 Drawing Sheets

OTHER PUBLICATIONS

Date, H., et al., Nature Genetics, 29(2): 184-188, XP-001172475, "Early-Onset Ataxia With Ocular Motor Apraxia and Hypoalbuminemia is Caused by Mutations in a New Hit Superfamily Gene", Oct. 2001.

Moreira, M.D.C., et al., Nature Genetics, 29(2): 189-193, XP-001172474, "The Gene Mutated in Ataxia-Ocular Apraxia 1 Encodes The New Hit/Zn-Finger Protein Aprataxin", Oct. 2001.

Dynal Catalog. Biomagnetic Techniques in Molecular Biology, 1998. pp. 8-9.

Hirano, et al., "Novel Splice Variants Increase Molecular Diversity of Aprataxin, the Gene Responsible for Early-Onset Ataxia with Ocular Motor Apraxia and Hypoalbuminemia," Neuroscience Letters, 366: 120-125 (2004).

Osada, et al., "Macaca Fascicularis Brain cDNA," Genbank Accession No. AB056422, Mar. 1, 2001.

* cited by examiner

FIG.1b

| Family | 2009 | 295 | 7 | 279 | 1462 | 666 | 9 |
|---|---|---|---|---|---|---|---|
| D9S1118 | 5 | 5 | | 6 | 6 | 7 | 6 |
| 462B18ms2 | 4 or 1 | 3 | 1 | | 5 | 5 | 4 |
| D9S165 | 1 | insT | insT | insT | | | 5 |
| aprataxin | 5 | 4 | 4 | 4 | P32L | P32L | P32L |
| D9S1788 | delT | 4 | 4 | 4 | 7 | 7 | 7 |
| D9S1845 | 3 | 9 | 9 | 9 | 4 | 4 | 4 |
| 126M6ms2 | 11 | 6 | 5 | 6 | 5 | 5 | 4 |
| D9S1878 | 5 | 9 | 8 | 3 | 8 | 8 | 8 |
| D9S1817 | 6 | 7 | 6 | 8 | 8 | 10 | 6 |
| D9S276 | 8 | 4 | nt | nt | 4 | 4 | (24) |

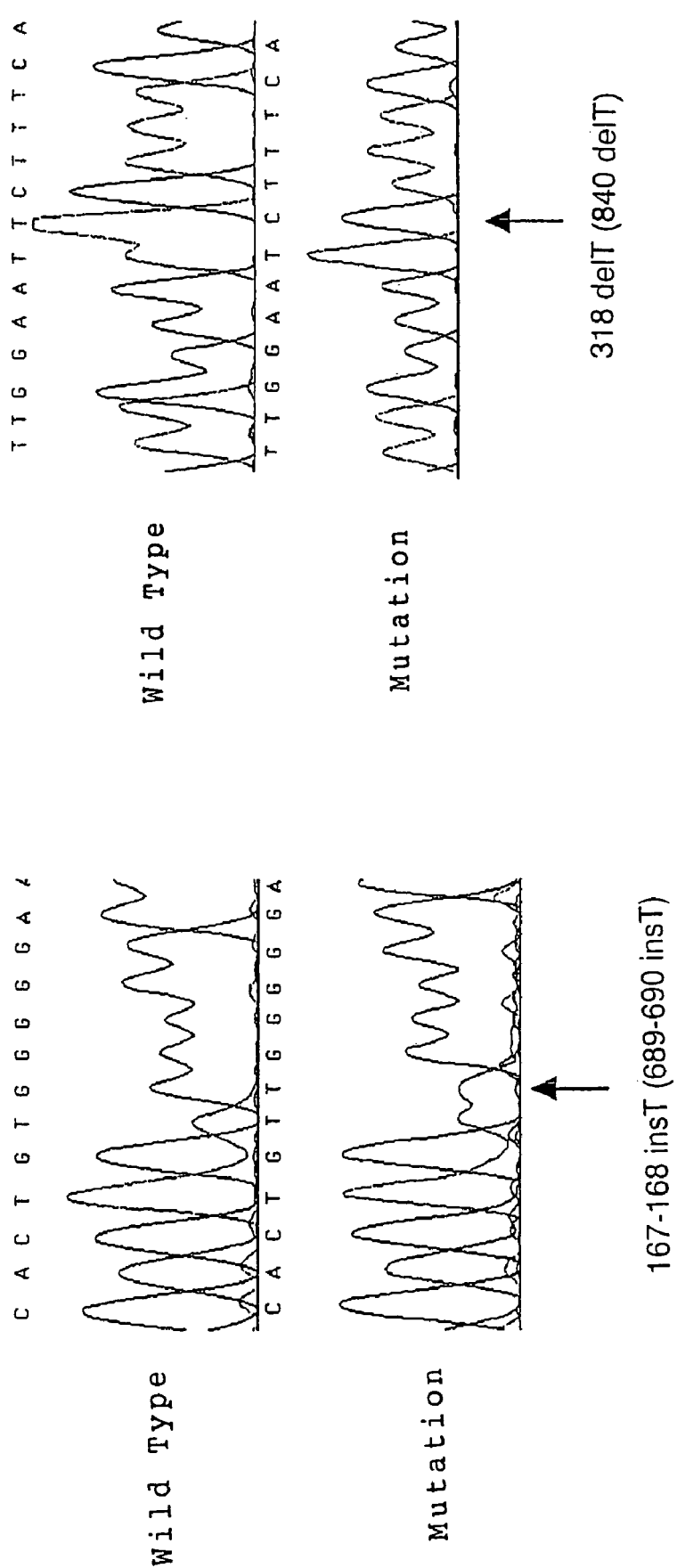

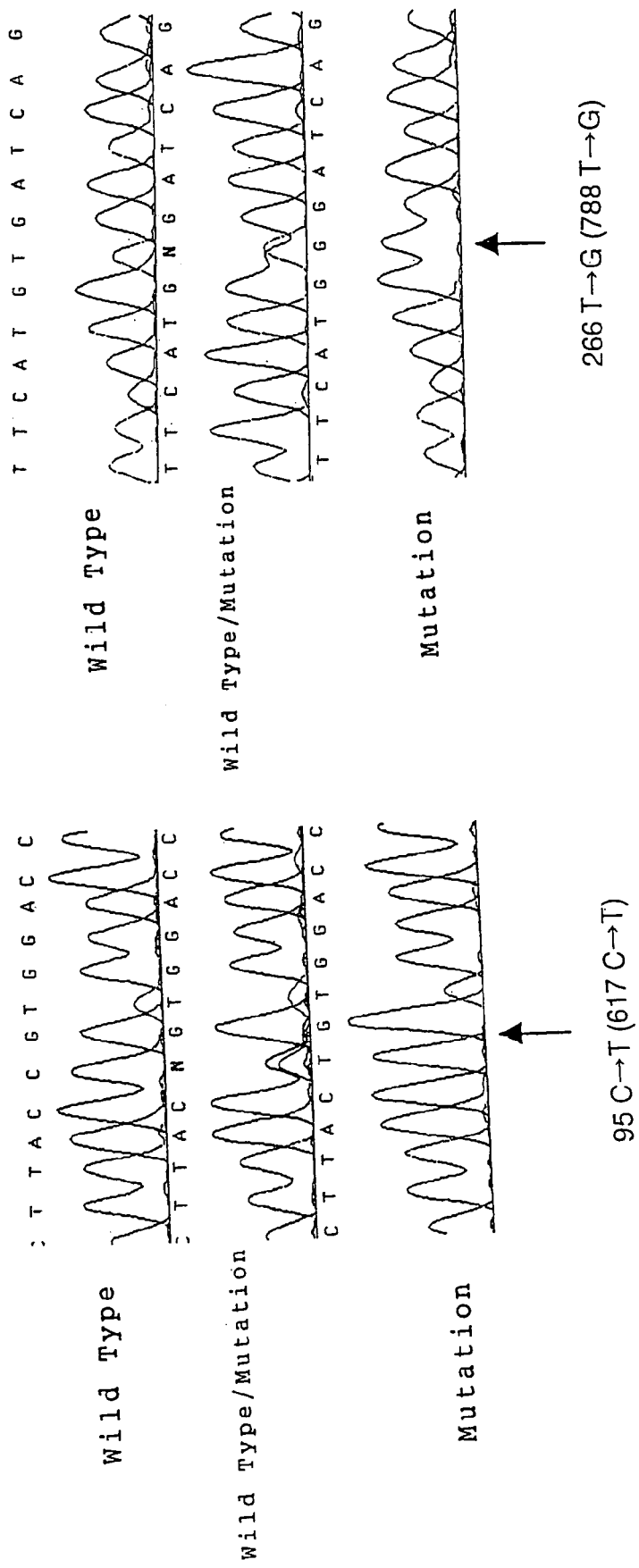

APPLICATION OF APRATAXIN GENE TO DIAGNOSIS AND TREATMENT FOR EARLY-ONSET SPINOCEREBELLAR ATAXIA (EAOH)

RELATED APPLICATIONS

This application is a divisional of U.S. application Ser. No. 10/209,609, filed Aug. 1, 2002, now U.S. Pat. No. 7,119,186, which claims priority under 35 U.S.C. §119 or 365 to Japan, Application No. 2001-279719, filed 14 Sep. 2001. The entire teachings of the above applications are incorporated herein by reference.

FIELD OF THE INVENTION

The present invention provides polynucleotides and proteins, which are involved in early-onset spinocerebellar ataxia with ocular motor apraxia and hypoalbuminemia (EAOH); and methods of using the polynucleotides and/or proteins to treat and/or diagnose EAOH.

BACKGROUND OF THE INVENTION

Friedreigh's ataxia (FRDA) is the most common autosomal recessive neurodegenerative disease among Caucasian populations. FRDA is characterized by the early onset of the disease usually before the age of 25, a progressive ataxia, sensory loss, absence of tendon reflexes and pyramidal weakness of the legs (Friedreich N, Virchows Arch. Pathol. Anat., 68, 145-245 (1876); Freidreich N, Virchows Arch. Pathol. Anat., 70, 140-142 (1877); Harding, A. E., Brain 104, 589-620 (1981); Durr, A. et al., N Engl J Med 335, 1169-75 (1996)). FRDA is known to be caused by a mutation of a gene on chromosome 9q13.

The inventor has recently identified a patient group which is characterized by autosomal recessive inheritance, early age of onset, FRDA-like clinical presentations, and hypoalbuminemia. Linkage of a causative gene of this disease to the FRDA locus was excluded by linkage analysis.

The clinical presentations of this disease were similar to those of a disease, which is called "ataxia with oculmotor apraxia, AOA" linked to 9p13 (do Ceu Moreira, M et al., Am J Hum Genet 68, 501-8 (2001)).

The causative gene for the disease, which the inventor has found has not yet been identified. Therefore, diagnosis of this disease has been based only on clinical observations.

SUMMARY OF THE INVENTION

The purpose of the present invention is to provide an application for a aprataxin gene, which is involved in a disease characterized by autosomal recessive inheritance, early age of onset, FRDA-like clinical presentations and hypoalbuminemia, that is, early-onset spinocerebellar ataxia with ocular motor apraxia and hypoalbuminemia (EAOH); and a protein encoded by the gene; a mutated aprataxin gene involved in the onset of EAOH a protein encoded by the mutated gene, treatment of the disease and diagnosis of the disease.

The inventor has confirmed that the novel disease is linked to the same locus as the above-mentioned AOA. Based on a strong linkage disequilibrium, the inventor has efficiently narrowed the candidate region of a causative gene. As a result, the inventor has identified the aprataxin gene as the causative gene, which belongs to a histidine triad (HIT) superfamily, and found a clear genotype-phenotype correlation.

Many HIT proteins have been previously identified. However, aprataxin is linked to a phenotype which differs from the phenotypes of these proteins.

The inventor has also found that early-onset spinocerebellar ataxia with ocular motor apraxia and hypoalbuminemia (EAOH) is caused by mutations in the aprataxin gene.

The present invention provides a protein comprising an amino acid sequence represented by SEQ ID NO: 2 or 4; or a protein comprising an amino acid sequence derived from the amino acid sequence of SEQ ID NO: 2 or 4 by deletion, substitution, or addition of one or more amino acids, which has functions equivalent to those of a human aprataxin protein, and being involved in the onset of EAOH; and fragments thereof.

The present invention also provides polynucleotide sequences or genes coding of the human aprataxin protein. Examples of such polynucleotide sequences are nucleotides 1 to 507 of SEQ ID NO: 1; a DNA hybridizing under stringent conditions to nucleotides 1 to 507 of SEQ ID NO: 1, and encoding a protein that has functions equivalent to those of a human aprataxin protein and is involved in the onset of EAOH; a nucleotide sequence which comprises nucleotide Nos. 7 to 1032 of the nucleotide sequence of SEQ ID NO: 3; a DNA hybridizing to nucleotides 7 to 1032 of SEQ ID NO: 3 and which encodes a protein that has functions equivalent to those of a human aprataxin protein and is involved in the onset of EAOH; and/or fragments thereof.

The present invention also provides vectors carrying one or more of the above polynucleotide sequences.

The present invention also provide mutated aprataxin polynucleotide sequences, which cause the onset of EAOH, or a fragment thereof which comprises at least one of the mutations. Examples of such mutated aprataxin polynucleotide sequences are substitution of a nucleotide 95 C of SEQ ID NO: 1 or 617 C of SEQ ID NO: 3 with T; insertion of T between a nucleotide 167 T of SEQ ID NO: 1 or 689 T of SEQ ID NO: 3 and a nucleotide 168 G of SEQ ID NO: 1 or 690 G of SEQ ID NO: 3; substitution of 266 T of SEQ ID NO: 1 or 788 T of SEQ ID NO: 3 with G; deletion of 318 T of SEQ ID NO: 1 or 840 T of SEQ ID NO: 3.

The present invention also provides methods for diagnosing the predisposition of an individual to early-onset spinocerebellar ataxia with ocular motor apraxia and hypoalbuminemia (EAOH) by detecting a mutation in an aprataxin polynucleotide obtained from the individual. Examples of such mutations include substitution of a nucleotide 95 C of SEQ ID NO: 1 or 617 C of SEQ ID NO: 3 with T; insertion of T between a nucleotide 167 T of SEQ ID NO: 1 or 689 T of SEQ ID NO: 3 and a nucleotide 168 G of SEQ ID NO: 1 or 690 G of SEQ ID NO: 3; substitution of 266 T of SEQ ID NO: 1 or 788 T of SEQ ID NO: 3 with G; deletion of 318 T of SEQ ID NO: 1 or 840 T of SEQ ID NO: 3.

Further, the present invention also provides a method of treating EAOH using the aprataxin gene or the aprataxin protein, and using the aprataxin gene or the aprataxin protein to manufacture a therapeutic agent for EAOH.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1a and 1b: show 7 pedigrees with EAOH.

FIGS. 5a-5d show the result of examining the nucleotide sequence of aprataxin gene using genomic DNAs of four patients with EAOH and a healthy individual.

DESCRIPTION OF SEQUENCES

SEQ ID NOS: 5 to 16: Synthesis

DETAILED DESCRIPTION OF THE INVENTION

A description of preferred embodiments of the invention follows.

1. To Obtain the Aprataxin Gene

Construction of a cDNA library, cloning and screening of the gene, and techniques for determining nucleotide sequences can be performed according to the methods described in literature known among persons skilled in the art, such as J. Sambrook, E. F. Fritsch & T. Maniatis (1989): Molecular Cloning, a laboratory manual, second edition, Cold Spring Harbor Laboratory Press, and Ed Harlow and David Lane (1988): Antibodies, a laboratory manual, Cold Spring Harbor Laboratory Press.

The gene of the present invention can be isolated by extracting mRNA and synthesizing cDNA. Human cells, such as lymphoblastic cells, can be used as a supply source of mRNA. mRNA can be prepared by extracting total RNA by, for example a guanidine thiocyanate/cesium chloride method, and obtaining poly(A)+ RNA (mRNA) by an affinity column method using oligo dT-cellulose or poly U-sepharose or by a batch method. Using the thus obtained mRNA as a template, a single-stranded cDNA is synthesized with an oligo dT primer and a reverse transcriptase, so that a double-stranded cDNA is synthesized from the single-stranded cDNA.

The synthesized double-stranded cDNA is incorporated into an appropriate vector, and then for example, *Escherichia coli* is transformed using the vector, thereby constructing a cDNA library and obtaining part of the gene of the present invention. Examples of selection methods include a plaque hybridization method, a colony hybridization method and an immuno-screening method, which use a probe synthesized based on a known cDNA sequence (EST has been reported as FLJ20157, NCBI Accession No. NM#017692) of this gene. The obtained cDNA fragment is amplified by PCR, and then the nucleotide sequence can be determined by the Maxam-Gilbert method (Maxam, A. M. and Gilbert, W., Proc. Natl. Acad. Sci. USA., 74, 560, 1977), the dideoxy method (Messing, J. et al., Nucl. Acids Res., 9, 309, 1981) and the like.

The full-length cDNA can be obtained by a RACE method (Rapid Amplification of cDNA ends), particularly by 5' RACE, using a primer prepared from the cDNA fragment.

Figure 2A:
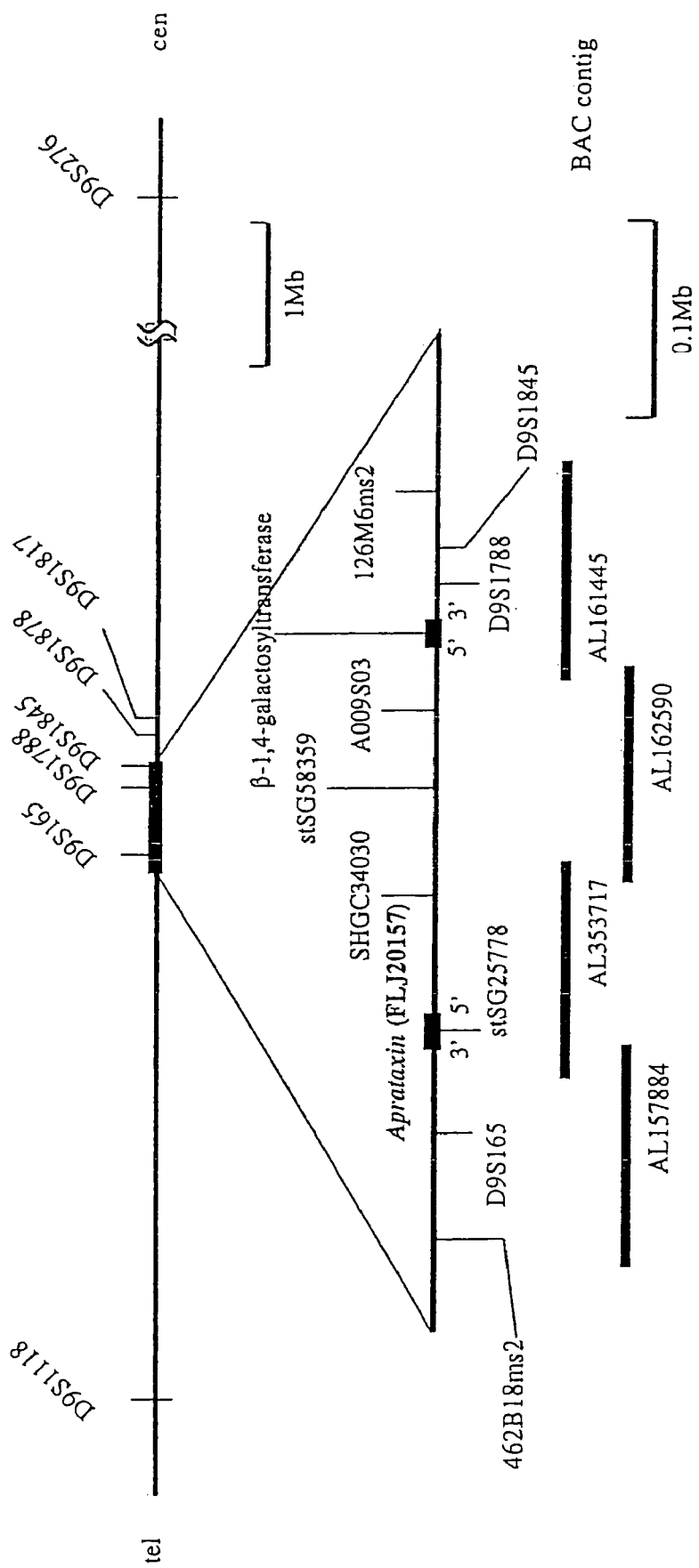
FIG. 2a shows physical maps of the short arm of chromosome 9.

Aprataxin gene has a genomic organization shown in FIG. 2, which contains two types of splicing patterns: a pattern (short form) which produces an aprataxin protein comprising 168 amino acids, and a pattern (long form) which produces an aprataxin protein comprising 342 amino acids including 174 amino acids added to the amino terminal side of the 168 amino acid aprataxin protein.

A nucleotide sequence represented by SEQ ID NO: 1 contains a cDNA encoding the exon portion of aprataxin gene, which expresses the aprataxin protein comprising 168 amino acids. In the nucleotide sequence, a nucleotide sequence of base positions 1 to 507 encodes the aprataxin protein comprising 168 amino acids. Further, a nucleotide sequence represented by SEQ ID NO: 3 contains cDNA which encodes the exon portion of an aprataxin gene that expresses the aprataxin protein comprising 174 amino acids added to the N-terminal side of the aprataxin protein. In the nucleotide sequence, a nucleotide sequence of base positions 7 to 1032 encodes the aprataxin protein comprising 342 amino acids.

The full-length sequence of an aprataxin gene containing the intron portion can be obtained based on the disclosure of the specification of the present invention and known gene information about the above EST.

The aprataxin gene used in the present invention may be either a full-length sequence containing introns or a DNA sequence containing only exons. In addition, partial sequences thereof may also be used in the present invention. Such partial sequences include those sequence that contain at least 15 nucleotides, including 20, 25, 30, 35, 40, 45, and 50 nucleotides of the polynucleotide sequences of the aprataxin genes.

Further, a DNA sequence that may also be used in the present invention is one which hybridizes under stringent conditions to a sequence containing the intron of an aprataxin gene or a cDNA sequence encoding the exon portion, or a partial sequence thereof, and encodes a protein having a function of an aprataxin protein. Here, a protein encoded by an aprataxin gene is referred to as an aprataxin protein.

The term "stringent conditions" means conditions under which a specific hybrid is formed and a non-specific hybrid is not formed. An example of such stringent conditions allows hybridization of DNAs sharing high homology, that is, 60% or more, preferably 80% or more, more preferably 90% or more homology, and allows no hybridization of nucleic acids having homology lower than the above homology. More specifically, such stringent conditions include a sodium concentration of 150 to 900 mM, preferably 600 to 900 mM, and a temperature of 60 to 68° C., preferably 65° C. Here, the term "function of an aprataxin protein" means a function of an aprataxin protein encoded by a wild type aprataxin gene, one of which is a function of HIT motif, that is, a function which enables the formation of a phosphate-binding loop. The term "having functions equivalent to" means that functions of an aprataxin protein are neither lost nor reduced, and do not cause the onset of EAOH. A DNA encoding an aprataxin protein having these functions is not identical to a mutated aprataxin gene encoding a protein which has causative mutations of EAOH and lacks or has reduced functions of an original aprataxin protein. Specifically, a mutant gene (167-168insT) in which T is inserted between 167 T and 168 G of the nucleotide sequence of the aprataxin gene of SEQ ID NO: 1; a mutant gene (95C→T) in which 95 C of the nucleotide sequence is substituted with T; a mutant gene (318delT) in which 318 T of the nucleotide sequence is deleted; and a mutant gene (266T→G) in which 266 T of the nucleotide sequence is substituted with G, do not possess functions equivalent to those of an aprataxin protein. Hence, these genes are not DNA which hybridizes under stringent conditions to a nucleotide sequence comprising nucleotide Nos. 1 to 507 of the nucleotide sequence represented by SEQ ID NO: 1 and encodes a protein having the functions of a human aprataxin protein and is involved in the onset of EAOH. Similarly, a mutant gene (689-690insT) in which T is inserted between 689 T and 690 G of the nucleotide sequence of the aprataxin gene of SEQ ID NO: 3; a mutant gene (617C→T) in which 617 C of the nucleotide sequence is substituted with T; a mutant gene (840delT) in which 840 T is deleted from the nucleotide sequence; and a mutant gene (788T→G) in which 788 T of the nucleotide sequence is substituted with G, are not DNA which hybridizes under stringent conditions to a nucleotide sequence comprising nucleotide Nos. 7 to 1032 of the nucleotide sequence represented by SEQ ID NO: 3 and encodes a protein having the functions of a human aprataxin protein and is involved in the onset of EAOH. Moreover, the term "(a protein) involved in the onset of EAOH" means it causes the onset of EAOH when a specific nucleotide is mutated.

Once the nucleotide sequence of a gene is determined, the gene of the present invention can be obtained by chemical synthesis or PCR using cloned cDNA as a template, or hybridization using a DNA fragment having the nucleotide sequence as a probe.

2. To Obtain a Aprataxin Protein

A protein of interest can be collected and purified by incorporating the obtained aprataxin gene into an available appropriate expression vector, transforming an appropriate host cell with the vector, culturing in an appropriate medium, and allowing expression of the protein. Any vector can be used, as long as it can replicate in a host cell, such as a plasmid, phage and virus. Examples of a vector include *Escherichia coli* plasmids, e.g., pBR322, pBR325, pUC118, pUC119, pKC30, and pCFM536, *Bacillus subtilis* plasmids, e.g., pUB110, yeast plasmids, e.g., pG-1, YEp13, and YCp50, and phage DNAs, e.g., λgt110 and λZAPII. Examples of a vector for mammal cells include virus DNA, e.g., baculo virus, vaccinia virus, adenovirus, SV40 and derivatives thereof. A vector may contain a replication origin, a selection marker and a promoter. If necessary, a vector may also contain an enhancer, a transcription termination sequence (terminator), a ribosome binding site, a polyadenylation signal and the like.

Examples of a host cell include cells of bacteria, e.g., *Escherichia coli, Streptomyces*, and *Bacillus subtilis*; fungal cells, e.g., strains of the genus *Aspergillus*; yeast cells, e.g., Baker's yeast, and methanol-assimilating yeast; insect cells, e.g., *Drosophila* S2 and *Spodoptera* Sf9; and mammal cells, e.g., CHO, COS, BHK, 3T3 and C127.

Transformation can be performed by known methods including a calcium chloride method, a calcium phosphate method, DEAE-dextran-mediated transfection, electroporation and the like.

The obtained recombinant protein can be separated and purified by various methods for separation and purification. For example, a method, or an appropriate combination of methods, such as ammonium sulfate precipitation, gel filtration, ion exchange chromatography or affinity chromatography can be used.

An amino acid sequence of the protein comprising 168 amino acids encoded by an aprataxin gene is represented by SEQ ID NO: 2; and an amino acid sequence of the protein comprising 342 amino acids encoded by an aprataxin gene is represented by SEQ ID NO: 4. These amino acid sequences may contain modifications including deletion, substitution, addition and the like of a plurality of, preferably several, amino acids as long as the proteins comprising the amino acid sequences have functions equivalent to those of an aprataxin protein. One to 10 amino acids, preferably 1 to 5 amino acids, more preferably 1 or 2 amino acids of the amino acid sequence represented by SEQ ID NO: 2 or 4 may be deleted; 1 to 10 amino acids, preferably 1 to 5 amino acids, more preferably 1 or 2 amino acids of the amino acid sequence represented by SEQ ID NO: 2 or 4 may be substituted with other amino acids; and 1 to 10 amino acids, preferably 1 to 5 amino acids, more preferably 1 or 2 amino acids may be added to the amino acid sequence represented by SEQ ID NO: 2 or 4.

Examples of such an amino acid sequence derived from the amino acid sequence represented by SEQ ID NO: 2 or 4 by deletion, substitution or addition of one or more amino acids have at least 60% or more, preferably 80% or more, and more preferably 95% or more homology with the amino acid sequence of SEQ ID NO: 2 or 4 when homology is calculated with BLAST.

The term "functions of an aprataxin protein" means the functions of an aprataxin protein encoded by a wild type aprataxin gene. One of the functions is a function of HIT motif to form a phosphate-binding loop. The term "having functions equivalent to" means that functions of an aprataxin protein are neither lost nor reduced, and do not cause the onset of EAOH. The above modifications including deletion, substitution, addition and the like of a plurality of, preferably several, amino acids are not identical to the mutation of amino acids caused by mutations in an aprataxin gene which causes EAOH, since the protein having these modifications retains the functions of an aprataxin protein. Specifically, an immature protein in which a frameshift mutation (167-168insT) occurs by insertion of T between 167 T and 168 G of the nucleotide sequence of the aprataxin gene of SEQ ID NO: 1; a mutant protein in which 95 C of the nucleotide sequence is substituted with T (95C→T), and an amino acid 32 of the aprataxin protein of SEQ ID NO: 2 is altered from Pro to Leu (P32L); an immature protein in which a frameshift mutation (318delT) occurs by deletion of 318 T of the nucleotide sequence; and a mutant protein (V89G) in which 266 T of the nucleotide sequence is substituted with G (266T→G) and an amino acid 89 of the aprataxin protein of SEQ ID NO: 2 is altered from Val to Gly comprise an amino acid sequence derived from the amino acid sequence represented by SEQ ID NO: 2 by deletion, substitution or addition of one or more amino acids, have functions equivalent to those of a human aprataxin protein, and do not correspond to proteins involved in the onset of EAOH. Similarly, an immature protein in which a frameshift mutation (689-690insT) occurs by insertion of T between 689 T and 690 G of the nucleotide sequence of the aprataxin gene of SEQ ID NO: 3; a mutant protein in which 617C of the nucleotide sequence is substituted with T (617C→T), and an amino acid 206 of the aprataxin protein of SEQ ID NO: 4 is altered from Pro to Leu (P206L); an immature protein in which a frameshift mutation (840delT) occurs by deletion of 840 T of the nucleotide sequence; and a mutant protein (V263G) in which 788 T of the nucleotide sequence is substituted with G (788T→G) and an amino acid 263 of the aprataxin protein of SEQ ID NO: 4 is altered from Val to Gly comprise an amino acid sequence derived from the amino acid sequence represented by SEQ ID NO: 4 by deletion, substitution or addition of one or more amino acids, have functions equivalent to those of a human aprataxin protein and do not correspond to proteins involved in the onset of EAOH. The term "(protein) involved in the onset of EAOH" means a protein which causes the onset of EAOH when mutation occurs at a specific nucleotide.

Accordingly, a gene that can be used in the present invention encodes a protein comprising the amino acid sequence represented by SEQ ID NO: 2 or 4, or encodes a protein comprising an amino acid sequence derived from the amino acid sequence represented by SEQ ID NO: 2 or 4 by deletion, substitution or addition of one or more amino acids and having functions of an apataxin protein.

3. To Obtain Apataxin Gene Containing Mutations which Cause EAOH

A DNA having a sequence containing a mutated site of an apataxin gene in which the nucleotide sequence contains mutations observed in EAOH patients; and a polypeptide containing an altered amino acid sequence encoded by DNA containing the mutated site can be used in the present invention. Here, the mutations in an apataxin gene which are observed in EAOH patients mean that a portion of the nucleotide sequence differs from that of a wild type apataxin gene and causes the onset of EAOH. Examples of mutations in a gene include substitution, insertion, deletion and the like of nucleotides. Gene mutation can be identified by diversified analysis of, for example, mutation frequency of an apataxin gene, transcription amount of apataxin mRNA, expression amount of an apataxin protein, altered functions of an apataxin protein and the like. Furthermore, the mutation can also be identified by analyzing the pedigrees of EAOH patients. Therefore, "the mutations in an apataxin gene" of the present invention includes mutations in an apataxin gene that may cause EAOH and is identified by these techniques. Examples of mutations found in EAOH patients, that is, an apataxin gene shown to contain mutations which cause EAOH, include a frameshift mutation (167-168insT) leading to expression of an immature protein in which T is inserted between 167 T and 168G of the nucleotide sequence of the apataxin gene of SEQ ID NO: 1; a mutation in which 95 C of the nucleotide sequence of an apataxin gene is substituted with T (95C→T), and an amino acid 32 of an apataxin protein is altered from Pro to Leu (P32L); a frameshift mutation (318delT), leading to expression of an immature protein, in which 318 T is deleted from the nucleotide sequence of an apataxin gene; a mutation in which 266 T of the nucleotide sequence of an apataxin gene is substituted with G (266T→G) and an amino acid 89 of an apataxin protein is altered from Val to Gly (V89G); a frameshift mutation (689-690insT) leading to expression of an immature protein, in which T is inserted between 689 T and 690 G of the nucleotide sequence of the apataxin gene of SEQ ID NO: 3; a mutation in which 617 C of the nucleotide sequence of an apataxin gene is substituted with T (617C→T), and an amino acid 206 of an apataxin protein is altered from Pro to Leu (P206L); a frameshift mutation (840delT) leading to expression of an immature protein in which 840 T of the nucleotide sequence of an apataxin gene is deleted; and a mutation in which 788 T of the nucleotide sequence of an apataxin gene is substituted with G (788T→G), and an amino acid at position 263 of an apataxin protein is altered from Val to Gly (V263G). A DNA or a protein having at least one of these mutated sites is included in the scope of the present invention.

These mutant genes can be isolated from EAOH patients, or can be obtained by introducing mutation into the apataxin gene obtained in 1.

To introduce a mutation into a gene, known methods, such as the Kunkel method, Gapped duplex method and the like, or methods based thereon can be employed. For example, mutation is introduced by site-directed mutagenesis using a kit for introducing mutation (e.g., Mutant-K (TAKARA) and Mutant-G (TAKARA)) or using LA PCR in vitro Mutagenesis series kit (TAKARA).

The technical scope of the present invention also includes DNA having a mutation, which is in a nucleotide sequence excluding the mutation site causing EAOH and which is not involved in the onset of EAOH, and hybridizing under stringent conditions to a mutant apataxin gene. The term "stringent conditions" means the above conditions.

4. Diagnosis of EAOH by Detection of Mutations in Apataxin Gene

Detection of the above causative mutations of EAOH in an apataxin gene enables diagnosis of patients and carriers having a mutant apataxin gene which is a causative gene for EAOH and prenatal diagnosis. Here, each, or plurality of mutations involved in the onset of EAOH that can be detected simultaneously include mutations 167-168insT or 689-690insT, 95C→T or 617C→T, 318delT or 840delT, and 266T→G or 788T→G. Insertion and deletion mutations, 167-168insT or 689-690insT, and 318delT or 840delT are known to be involved in early onset; and missense mutations, 95C→T or 617C→T, and 266T→G or 788T→G are known to be involved in relatively late onset. Hence, detection of types of mutations enables prediction of the time of onset. Further, analysis of mutations using individual EAOH patients has revealed the presence of examples simultaneously having two mutations; 167-168insT or 689-690insT and 95C→T or 617C→T; two mutations, 167-168insT or 689-690insT and 318delT or 840delT; and two mutations, 95C→T or 617C→T and 266T→G or 788T→G. These two mutations may be detected at the same time.

As biological samples for diagnosis, nucleic acids derived from any tissue cells of individuals to be diagnosed can be used. Nucleic acids preferably used herein are derived from peripheral leucocytes, villus, and suspended cells of amnionic fluid. DNA used as a sample may be either genomic DNA or cDNA.

Mutations in an apataxin gene causing EAOH can be detected by measuring qualitatively or quantitatively the presence, expression and mutation of an apataxin gene DNA or RNA in each tissue by PCR, Northern hybridization, quantitative PCR, RT-PCR, in situ hybridization, FISH and the like.

(1) Detection of Mutant Apataxin Gene Causing EAOH

Detection of the presence of mutations in an apataxin gene causing EAOH enables direct detection of mutations in an apataxin gene. Alternatively, absence of a wild type DNA having no mutation in the apataxin gene which causes EAOH may be detected. In the latter case, confirmed diagnosis of EAOH can be made by showing homozygosity for a mutant apataxin gene or complex heterozygosity for different types of mutations in an apataxin gene.

For example, first a probe complementary to a nucleotide sequence containing a mutant nucleotide portion of a mutant apataxin gene, and a probe complementary to a nucleotide sequence corresponding to the mutant nucleotide portion of a wild type gene are prepared. The length of a probe to be used is not limited, and it may be the full length of a nucleic acid fragment to be amplified by the nucleic acid amplification method described later. Normally, the probe is preferably 15 bp to 50 bp, more preferably, 18 bp to 30 bp long. Probes labeled with radioactive isotopes, fluorescent materials, enzyme or the like can be used. Next, a gene fragment containing the mutant nucleotide portion in a specimen is amplified by the nucleic acid amplification method, and then the amplified fragment and the probe are allowed to react.

Whether the aprataxin gene is a wild type or a mutant can be detected by examining if DNA in the specimen hybridizes to which mutant probe. Primers that can be used for nucleic acid amplification are sequences complementary to the end portions of a region to be amplified which flank the EAOH-causing aprataxin gene mutation at the both sides of the mutation. The number of nucleotides in the region to be amplified is not limited, and it may be several ten to several hundred nucleotides. The length of nucleotides to be amplified may be set in an amplification region so as to contain only one mutation or two or more mutations of an aprataxin gene involved in EAOH. The amplification region may contain exons only, or may contain introns. When cDNA is used as a sample, the amplification region preferably contains exons only, but when genomic DNA is used as a sample and the length of nucleotides to be amplified exceeds the length of exons, the region preferably contains introns. Moreover, a primer can be set in a region containing a mutated site. The length of a primer is not limited, and is preferably 15 bp to 50 bp, more preferably 20 bp to 30 bp.

(2) Detection of Mutations Causing EAOH by Measuring Transcription of mRNA from Aprataxin Wild Type Gene or Mutant Gene.

Mutations in an aprataxin gene can be detected by measuring quantitatively or qualitatively transcription of mRNA from a mutant DNA or a wild type DNA.

For example, insertion and deletion mutations in an aprataxin gene result in a frameshift mutation which produces immature mRNA and decreased amount of mRNA transcribed from a wild type aprataxin gene. Hence, when a significant decrease in mRNA level is found, mutations in an aprataxin gene can be detected.

The amount of mRNA can also be measured by Northern blotting. Further, the amount of cDNA may be measured after synthesis of cDNA.

(3) Detection of Mutations in an Aprataxin Gene by Measuring Aprataxin Protein

Gene mutation can be detected by measuring the molecular amount of aprataxin gene products or a mutant protein using antibodies which allows recognition of amino acid mutations due to missense mutations.

5. Treatment of EAOH Using Aprataxin Gene or Aprataxin Protein

DNA or RNA nucleotides containing the sequence of the aprataxin gene of the present invention can be applied to treat EAOH by gene therapy technology.

For example, a protein encoded by an aprataxin gene is expressed in vivo, so that EAOH can be suppressed. For administration, DNA or the like containing an aprataxin gene sequence may be introduced into vectors which can be used for gene therapy including adenovirus vectors, adeno-associated virus vectors, herpes virus vectors, retrovirus vectors, and lentivirus vectors. In addition, DNA or the like can be directly introduced by, e.g., injection, or introduced by a gene gun method. Administration may be performed orally or by injection. Any manner of administration can be used as long as it can introduce DNA in vivo. Further, an aprataxin gene or a vector containing an aprataxin gene can be directly administered in vivo.

Further, an aprataxin protein can be used for treating EAOH.

Therefore, the scope of the present invention also includes the therapy for EAOH using an aprataxin gene or an aprataxin protein. Furthermore, the aprataxin gene or the aprataxin protein of the present invention can be used for manufacturing therapeutic agents for EAOH.

Therapeutic, pharamaceutical preparations containing DNA or RNA which contains the sequence of an aprataxin gene, or a protein encoded by an aprataxin gene may contain a pharmaceutically permissible carrier. Examples of pharmaceutically permissible carriers that can be used herein include oral liquid preparations, such as a suspension and a syrup, for example, water; saccharides, e.g., sucrose, sorbitol and fructose; glycols, e.g., polyethylene glycol and propylene glycol; oils, e.g., sesame oil, olive oil and soybean oil; and antiseptics, e.g., p-hydroxybenzoic acid ester. Examples of powder, pills, capsules and tablets that can be used herein include fillers, e.g., lactose, glucose, sucrose and mannitol; disintegrators, e.g., starch and sodium alginate; lubricants, e.g., magnesium stearate and talc; binders, e.g., polyvinyl alcohol, hydroxypropylcellulose and gelatin; surface active agents, e.g., fatty acid ester; and plasticizers, e.g., glycerine. Moreover, a solution for injection can be prepared using a carrier comprising distilled water, salt solution, glucose solution and the like. At this time, the solution for injection can be prepared as a solution, suspension, or a dispersant using an appropriate solubilizer and a suspending agent according to standard techniques.

A dose and a dosage schedule may be appropriately determined depending on the age, condition, sexuality and severity of the disease of a patient. A dose may be a therapeutically effective amount.

The following Examples provide an illustration of embodiments of the invention and should not be construed to limit the scope of the invention, which is set forth in the appended claims.

EXAMPLES

Example 1

Collection of Genomic DNA and Isolation of Genomic DNA and RNA

Genomic DNA were collected from 28 individuals, including 15 affected individuals from 7 families with EAOH, for linkage analysis after obtaining their informed consent (Koike, R. et al., Neurological Medicie 48, 237-242 (1998); Uekawa, K. et al., Rinsho Shinkeigaku 32, 1067-74 (1992); Kubota, H. et al, J Neurol Sci 158, 30-7 (1998); Sekijima, Y. et al., J Neurol Sci 158, 30-7 (1998); Fukuhara, N. et al., J Neurol Sci 133, 140-51 (1995); Kawasaki, S., et al, Rinsho Shinkeigaku 22, 15-23 (1982)). Consanguineous marriage is present in three families and affected individuals were found only among siblings, indicating autosomal recessive mode of inheritance. The affected individuals of each family were clinically examined by two or more neurologists from five different institutions. In addition, genomic DNAs were also collected from affected individuals from 15 pedigrees, diagnosed as having EAOH, FRDA or AOA, for mutational analysis after obtaining their informed consent (Aicardi, J. et al., Ann Neurol 24, 497-502 (1988); Inoue, N. et al., Rinsho Shinkeigaku 11, 855-861 (1971); Araie, M. et al., Jpn J Opthalmol 21, 355-365 (1977)).

High-molecular-weight genomic DNA was prepared from peripheral white blood cells according to standard protocols (Sambrook, J. et al., Molecular Cloning: a laboratory manual 3rd ed., Vol. 1 6.4-6.12 (Cold Spring Harbor, N.Y., 2001)). We extracted total RNA from lymphoblastoid cell lines of an EAOH patient using the RNeasy kit (Qiagen) according to the manufacturer's instructions.

Example 2

Linkage Analysis

Linkage analysis was carried out using microsatellite markers on 9p13, including D9S1118, D9S165, D9S1788, D9S1845, D9S1817 and D9S276. To carry out detailed linkage disequilibrium analysis, we developed two new microsatellite markers (462B18 ms2 and 126M6 ms2) by searching for short tandem repeats in databases.

The following primer pairs were designed for these new markers: 126M6 ms2 (forward primer, 5'-ATGTG-GAGAAATTGGAGGCA-3' (SEQ ID NO: 5) and reverse primer, 5'-TGTGAAGGAATTGAGCTGGT-3' (SEQ ID NO: 6)), and 462B18 ms2 (forward primer, 5'-TGGGTTTTGAT-GTGCTTCCA-3' (SEQ ID NO: 7) and reverse primer, 5'-GAAGCAGGTAGAAGAGGAGT-3' (SEQ ID NO:8)).

Physical maps including BAC contig, ESTs, cDNAs, genomic nucleotide sequences and microsatellite markers were constructed based on the Human Genome Recognition Project: HGREP (Institute of Medical Science, University of Tokyo hgrep.ims.u-tokyo.acjp/cgi-bin/HTG_tool/view.cgi?layer=top), Sanger Centre human Chromosome 9 Project (www.sanger.ac.uk/HGP/Chr9) and Marshfield Medical Research Foundation (www.marshmed.org/genetics/). Exon-intron structures were deduced by comparing the nucleotide sequences of FLJ20157 and a BAC clone, AL353717.

Figure 1A:
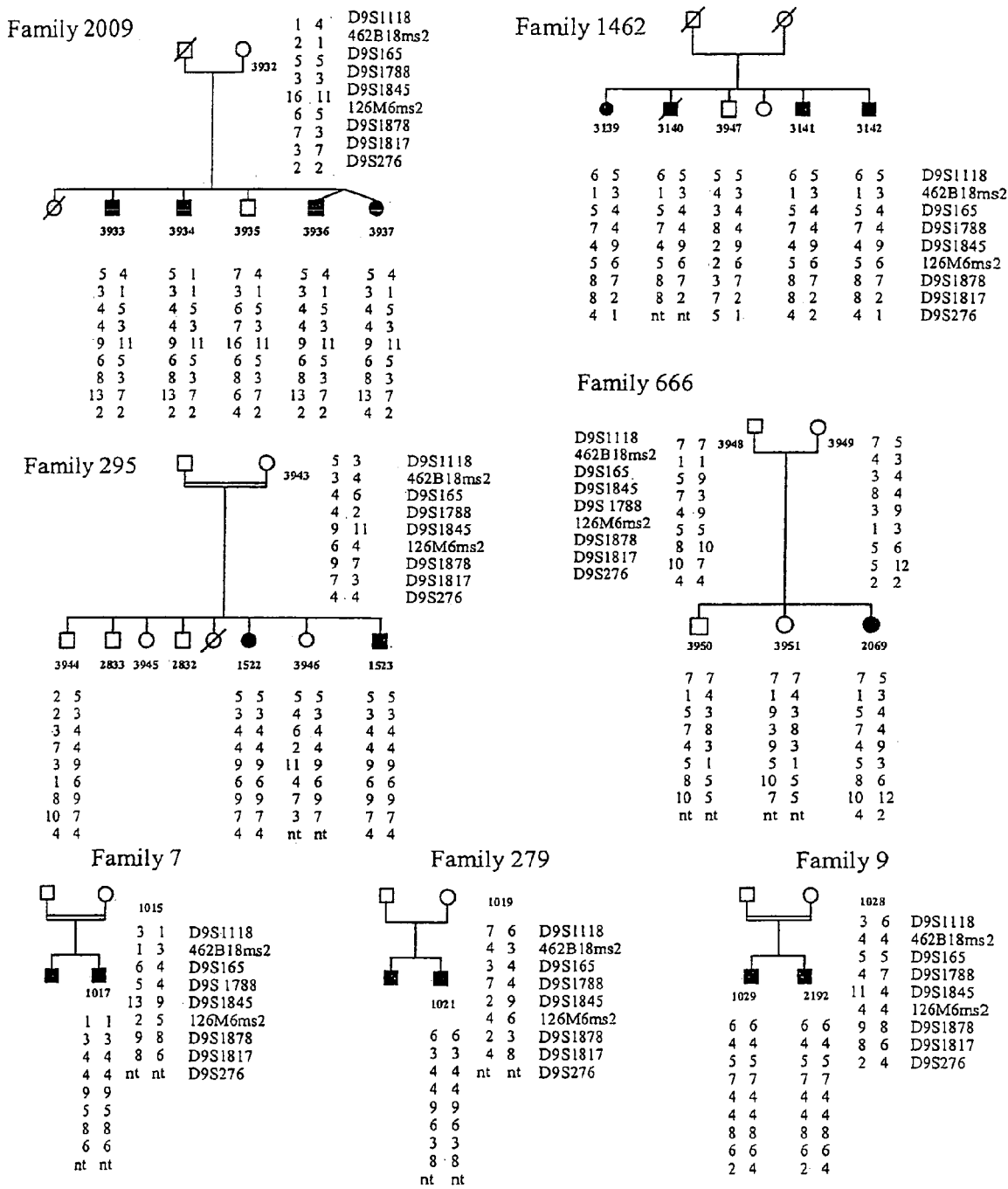

FIG. 1a shows pedigree charts of the seven Japanese EAOH families linked to the short arm of chromosome 9. In the figure, a box symbol represents males and a circular symbol represents females. A solid symbol represents a patient. Haplotypes at D9S1118, 462B18ms2, D9S165, D9S1788, D9S1845, 126M6 ms2, D9S1878, D9S1817 and D9S276 are shown. The alleles, whose phases were unequivocally determined, are shown in parentheses. FIG. 1b shows haplotypes cosegregating with EAOH in the seven Japanese EAOH families. The haplotypes shared among the seven families are shaded in blue and pink.

Pair-wise lod scores were calculated using the MLINK program of LINKAGE (version 5.2)) (Lathrop, G. M. et al., Am J Hum Genet 36, 460-5 (1984); Lathrop, G. M. et al., Am J Hum Genet 37, 482-98 (1985)) and the FASTLINK 4.1P package. Autosomal recessive inheritance with a complete penetrance by the age of 20 and a disease gene frequency of 0.001 were assumed in the calculation. Allele frequencies for markers were determined by the analysis of at least 37 unrelated Japanese individuals. Haplotypes were determined to minimize the number of recombination events using the GENEHUNTER program 2.0 beta (Cottingham, R. W. et al., Am J Hum Genet 53, 252-63 (1993); Kruglyak, L. et al., Am J Hum Genet 58, 1347-63 (1996)).

Analysis of microsatellite makers on 9p13 revealed the highest cumulative pair-wise lod score of 7.71 at D9S1845 ($\theta$=0) (Table 1)

Table 1: Two-point lod score table for seven loci on the short arm of chromosome9

Recombination Fraction

By analyzing additional markers, recombination events were found in affected individuals at D9S1118, the telomeric boundary and D9S276, the centromeric boundary (FIG. 1). Three disease-haplotypes linkages (defined by markers at D9S165, D9S1788 and D9S1845) were found in the seven families, suggesting a strong linkage disequilibrium. Decay of linkage disequilibrium was observed at 462B18 ms2 and 126M6 ms2 (FIG. 1). These results indicate that the causative gene is probably located in the 350 kb segment between these markers (FIG. 2).

It is confirmed that the four expressed sequence tags (ESTs) and two genes are present in this region of 9p13 (FIG. 2) and only the EST stSG25778 (part of FLJ20157 mRNA (NCBI Accession No. NM_017692)) is expressed in the central nervous system.

Figure 2B:
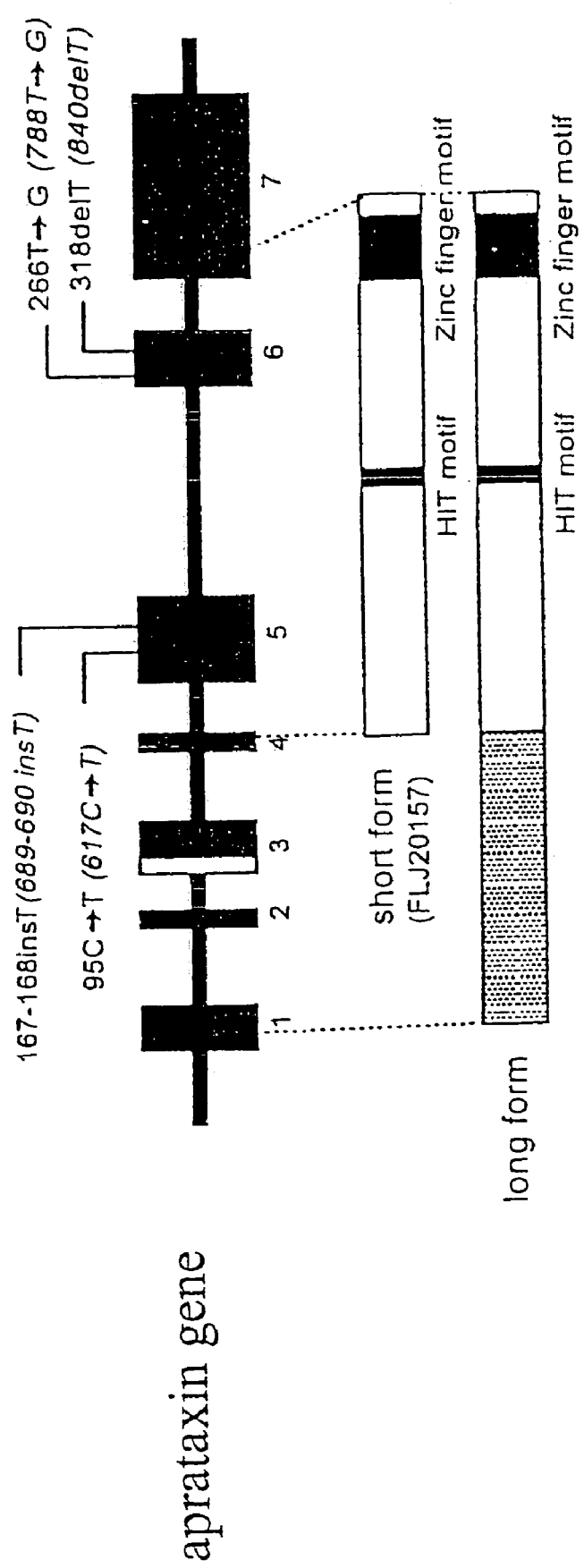
FIG. 2b shows genomic organization of the aprataxin gene.

FIG. 2 shows physical maps of the genomic DNA containing the critical region of the EAOH gene and genomic organization of the aprataxin gene. FIG. 2b shows positions of the marker loci flanking the EAOH candidate region on the short arm of chromosome 9 (9p13). In the 350 kbp segment, two genes and four expressed sequence-tagged sites were identified. The BAC contig between 462B18ms2 and 126M6 ms2 is shown under the physical map. FIG. 2b

| Locus | 0 | 0.01 | 0.05 | 0.1 | 0.2 | 0.3 | 0.4 | $Z_{max}$ | $\theta_{max}$ |
|---|---|---|---|---|---|---|---|---|---|
| D9S1118 | — | 3.1 | 3.82 | 3.58 | 2.56 | 1.45 | 0.52 | 3.82 | 0.05 |
| D9S165 | 6.49 | 6.34 | 5.72 | 4.94 | 3.4 | 1.9 | 0.7 | 6.49 | 0 |
| D9S1788 | 5.12 | 4.99 | 4.45 | 3.79 | 2.54 | 1.40 | 0.4 | 5.12 | 0 |
| D9S1845 | 7.71 | 7.53 | 6.8 | 5.88 | 4.05 | 2.30 | 0.82 | 7.71 | 0 |
| D9S1878 | 7.19 | 7.02 | 6.3 | 5.41 | 3.65 | 2.01 | 0.66 | 7.19 | 0 |
| D9S1817 | 5.75 | 5.58 | 5.2 | 4.52 | 3.08 | 1.72 | 0.59 | 5.75 | 0 |
| D9S276 | — | -1.24 | -0.07 | 0.26 | 0.35 | 0.22 | 0.07 | 0.59 | 0.23 | shows genomic organization of the aprataxin gene. Four mutations were found in exons 5 and 6.

Example 3

Mutation Analysis

All the coding exons of FLJ20157 were amplified and mutations were analyzed. FLJ20157: cds1 forward primer 5'-TTC ACA AGC AAC CCA GAA TA-3' (SEQ ID NO:9) reverse primer 5'-CCG TGA GAA TTA GTG GAG TT-3' (SEQ ID NO:10), cds2 forward primer 5'-GTG AAA ACC AAG GAA CAC Tg-3' (SEQ ID NO:11) reverse primer 5'-TAT AGG AAG GCA ATG GAG Tg-3' (SEQ ID NO:12), cds3 forward primer 5'-GGG TCT CAG TGC AAT ATG Tg-3' (SEQ ID NO: 13) reverse primer 5'-ATT TCA GTG CTC TCC TCT CT-3' (SEQ ID NO: 14), cds4 forward primer 5'-TCT GTG GAG TGG TCA TTT AC-3' (SEQ ID NO: 15) reverse primer 5'-TAT AGG AAG GCA ATG GAG Tg-3' (SEQ ID NO:16)

PCR reactions consisted of an initial denaturation step of 3 min at 95° C., amplification with denaturation for 30 cycles of 30 s at 95° C., annealing for 30 s at 55° C. and extension for 1 min at 72° C., followed by a final extension step for 10 min at 72° C.

PCR products were separated by agarose gel electrophoresis and purified them using a QIAquick Gel Extraction Kit (Qiagen). The purified PCR products (30-60 ng) were then subjected to cycle sequence reactions using Big Dye terminators (DNA sequencing kit, PE Applied Biosystems). The reaction products were purified using a DyeEx Spin kit (Qiagen) and analyzed them using an ABI377 DNA sequencer (PE Applied Biosystems).

The mutation analysis of FLJ20157 revealed three independent mutations in all seven families (FIG. 2 and Table 2).

TABLE 2

Aprataxin mutations and the associated haplotypes in 22 Japanese families.

| Mutation | D9S1788-D9S1845-D9S165 | Protein | Pedigrees |
|---|---|---|---|
| n771(insT) | 4-9-4 | frameshift | 295, 7, 279, 293, 1108, 1306, 2007, 2014, 2021, 1915, 1802, 1869, 2029, 2058, 2059, 9, 1993 |
| nt669 (C T) | 7-4-5 | P32L | 9, 1993 |
| nt771 (insT) & nt669 (C T) | 4-9-4/7-4-5 | frameshift & P32L | 1462, 666 & |
| nt771 (insT) & nt923 (delT) | 4-9-4/3-11-5 | frameshift | 2009 |
| NT870 (T G) & nt669 (C T) | 5-17-5/7-4-5 | P32L & V89G | 2637 |

Aprataxin mutations were identified in 22 EAOH pedigrees including those previously reported as AOA. The numbers for AOA pedigrees are shown in italic. The numbers for the seven EAOH pedigrees which were subjected to linkage analysis are shown in bold.

It was found that affected individuals of pedigrees 295, 7 and 279 who carry the 4-4-9 haplotype in the homozygous state are also homozygous with respect to an insertion mutation, 167-168insT, which results in a frameshift with a premature stop codon at the amino acid residue 96. The same mutation is observed in the heterozygous state in affected individuals from pedigrees 1462, 666 and 2009.

The next most common mutation was a C-to-T transition (P32L), which is associated with the 5-7-4 (D9S165-D9S1788-D9S1845) haplotype in pedigrees 9, 1462 and 666.

A single-nucleotide deletion (318delT) resulting in a frameshift with a premature stop codon at the amino acid residue 115 in pedigree 2009 was observed. Affected individuals from pedigrees 1462, 666 and 2009 have these mutations in the compound heterozygous state.

Any of these mutations was not found in 200 unrelated Japanese controls.

An additional 13 pedigrees with mutations in the FLJ20157 were also identified. The patients of these pedigrees showed similar clinical presentations (Table 2).

The linkage to 9p13 was originally described for families with AOA (do Ceu Moreira, M et al., Am J Hum Genet 68, 501-8 (2001)). Ocular motor apraxia is characterized by impaired initiation of saccade eye movement and patients often use head thrusts to compensate for the impaired initiation of saccade (Cogan D., Am J Ophthalmol 36, 433-441 (1953)). Ocular motor apraxia is the prominent clinical presentation in AOA (do Ceu Moreira, M et al., Am J Hum Genet 68, 501-8 (2001); Aicardi, J. et al., Ann Neurol 24, 497-502 (1988); Barbot, C. et al., Arch Neurol 58, 201-5 (2001)), while hypoalbuminemia is the hallmark of disease in the families described here (koike, R et al., Neurological Medicie 48, 237-242 (1988); Uekawa, K. et al., Rinsho Shinkeigaku 32, 1067-74 (1992)). To explore the possibility that both conditions are caused by mutations in the FLJ20157 gene, we analyzed two pedigrees previously reported as having AOA (Aicardi, J. et al., Ann Neurol 24, 497-502 (1988); Inoue, N. et al., Rinsho shinkeigaku 11, 855-861 (1971); Araie, M. et al., Jpn J Opthalmol 21, 355-365 (1977); Kurita-Takahashi, S. et al., Neuro-ophthalmology 12, 41-45 (1991)). One of the families was described in an original paper proposing AOA as a new disease entity (Aicardi, J. et al., Ann Neurol 24, 497-502 (1988)). Interestingly, the same 167-168insT mutation was identified in the pedigrees 2014 and 2021 (Table 2). The AOA patients were 8 and 12 years old when they were first described in the literature. Re-examination of the two patients at ages 48 and 28 shows that their head thrust was much milder than previously described and that both had hypoalbuminemia, indicating that clinical presentations vary considerably with age.

The inventor proposes the name, "early-onset ataxia with ocular motor apraxia and hypoalbuninemia (EAOH)" for this unique neurodegenerative disease. The clinical presentation of EAOH have similarities to those of FRDA. Ocular motor apraxia and hypoalbuminemia are the hallmarks that differentiate EAOH from FRDA (Friedrich N, Virchows Arch. Pathol. Anat., 68, 145-245 (1876); Freidrich N, Virchows Arch. Pathol. Anat., 70, 140-142 (1877); Harding, A. E., Brain 104, 589-620 (1981); Durr, A. et al., N Engl J Med 335, 1169-75 (1996)) or AVED (Gotoda, T. et al., N Engl J Med 333, 1313-8 (1995); Ouahchi, K et al., Nat Genet 9, 141-5 (1995)). Also, there is an obvious genotype-phenotype correlation. The insertion or deletion mutations result in a severe phenotype with onset in childhood, and ocular motor apraxia is the predominant muerological sign. Missense mutations, however, lead to a mild phenotype with a relatively late age of onset (the age of onset for pedigree 2637 is 25 years).

FIG. 5 is aprataxin gene sequence obtained by using genomic DNA from 4 EAOH patients and a normal. Another mutation was detected for each of the 4 EAOH patients.

The inventors named the causative gene of the disease of which major clinical features are ataxia, ocular motor apraxia and hypoalbuminemia as aprataxin (APTX).

Example 4

Northern-Blot Analysis

A $^{32}$P-labeled cDNA probe from the full-length FLJ20157 cDNA clone was generated using Ready-To-Go DNA Labeling Bead (Amersham Pharmacia Biotec). The probe was hybridized on Northern blot membrane [human adult multiple tissue northern blot, human brain multiple tissue northern blot II and human brain multiple tissue northern blot IV (Clontech)]. Relative radioactivities of aprataxin and GAPDH mRNA bands were measured with a Fuji Bioimage Analyzer (BAS2000) using an erasable phosphor imaging plate.

Figures 3A, 3B:
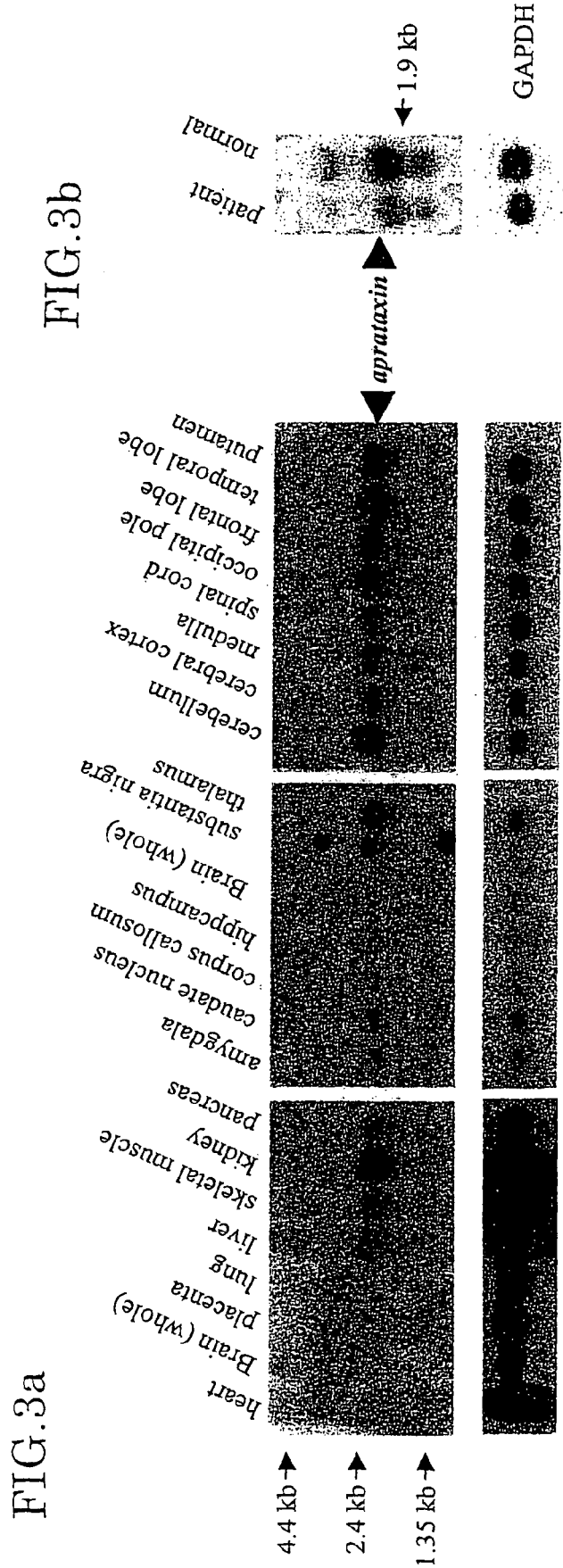
FIGS. 3a and 3b show the result of analysis of aprataxin gene expression in human tissues.

FIG. 3 shows the analysis of aprataxin gene expression in human tissue. FIG. 3a shows multiple-tissue Northern blot membranes probed with the human FLJ20157 cDNA probes. A 2.2 kb aprataxin transcript was detected in all the tissues. In addition, a shorter band (1.35 kb) was detected. The smaller band was detected under highly stringent hybridization condition, raising the possibility that the smaller band is splicing variant. FIG. 3a (below) shows the result of the detection using GAPDH cDNA as a loading control after deprobing.

FIG. 3b shows ataxin gene expression in lymphoblastoid cell lines from an EAOH patient (patient No. 3936 in pedigree 2009). Total RNA was isolated from EBV-transformed lymphoblastoid cell lines and Northern blot hybridization was performed with human FLJ20157, followed with GAPDH cDNA.

The northern blot analysis revealed that ataxin mRNA was present ubiquitously as 2.2 kb mRNA, and at 57% of the normal level in lymphoblastoid cell lines from a patient carrying 167-168insT and 318delT (FIG. 3). The reduction in mRNA level is occasionally observed in frameshift mutations that lead to premature stop codons.

Example 5

Sequence Analysis, Alignment and Construction of Phylogenetic Tree

Amino acid homology search were performed using a standard protein-protein BLAST. Deduced amino-acid sequences of ataxin (NCBI accession NP_060162 or XP_005534), mouse ortholog of ataxin (NCBI accession NP_079821), human HINT (NCBI accession NP_005331), mouse HINT (Gene Bank accession AAC1076), fly AAF51208 (GeneBank accession AAF1208), yeast HINT (NCBI accession NP_010158), human FHIT (NCBI accession NP_002003) and mouse FHIT (NCBI accession NP_034346) were multiply aligned using the ClustalW program, version 1.81 with default parameters (Thompson, J. D. et al., Nucleic Acids Res 22, 4673-80 (1994)). The phylogenetic tree was constructed based on the entire edited alignment using the Neighbor-joining method (Saitou, N. et al., Mol Biol Evol 4, 406-25 (1987)) and was drawn using the TreeView 1.6.5 program.

Figure 4A:
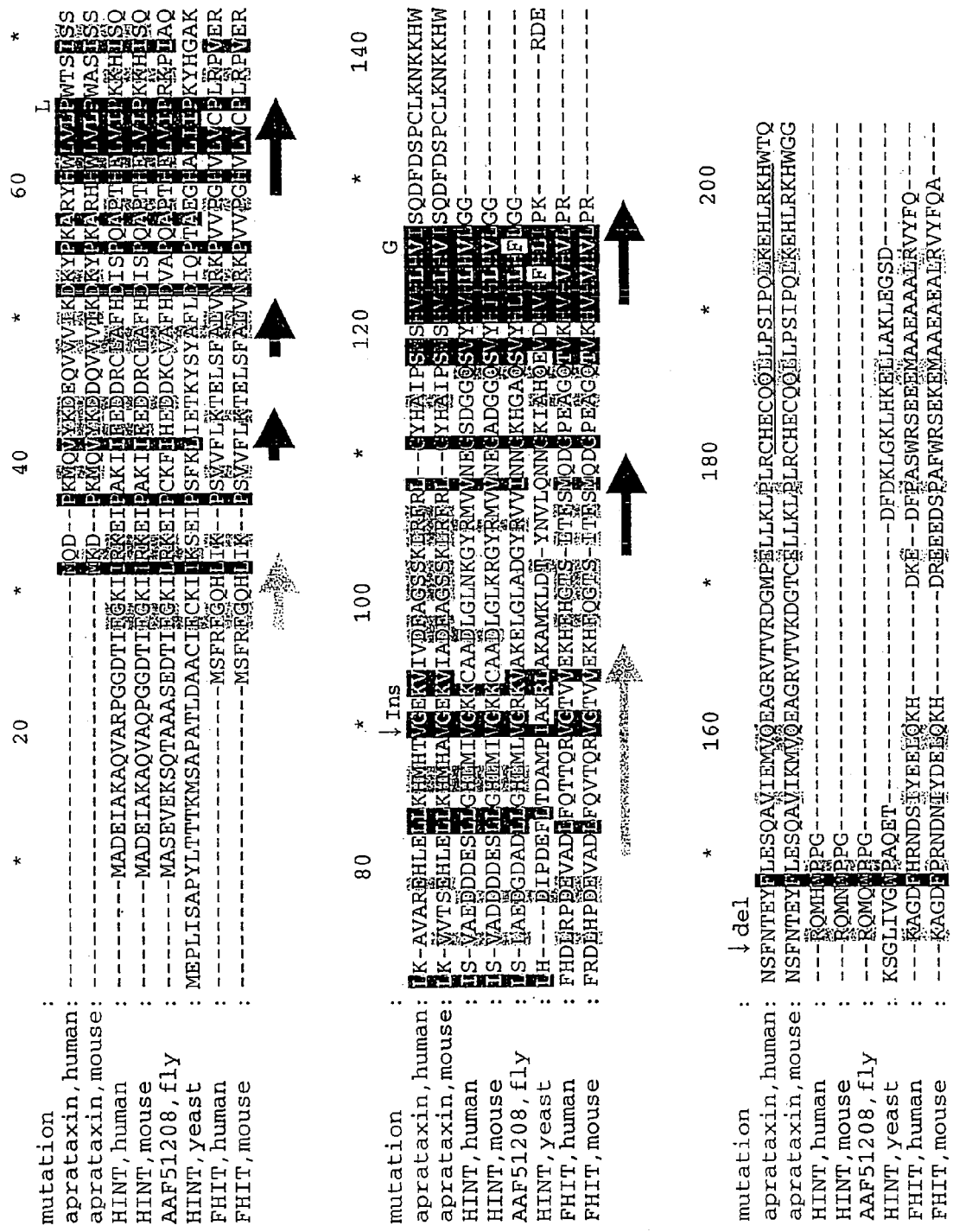
FIG. 4a shows multiple amino acid sequence alignment of aprataxin with HIT superfamily proteins—human aprataxin is SEQ ID NO:17; mouse aprataxin is SEQ ID NO:18; human HINT is SEQ ID NO:19; mouse HINT is SEQ ID NO:20; fly AAF51208 is SEQ ID NO:21; yeast HINT is SEQ ID NO:22; human FHIT is SEQ ID NO:23; mouse FHIT is SEQ ID NO:24.
Figure 4B:
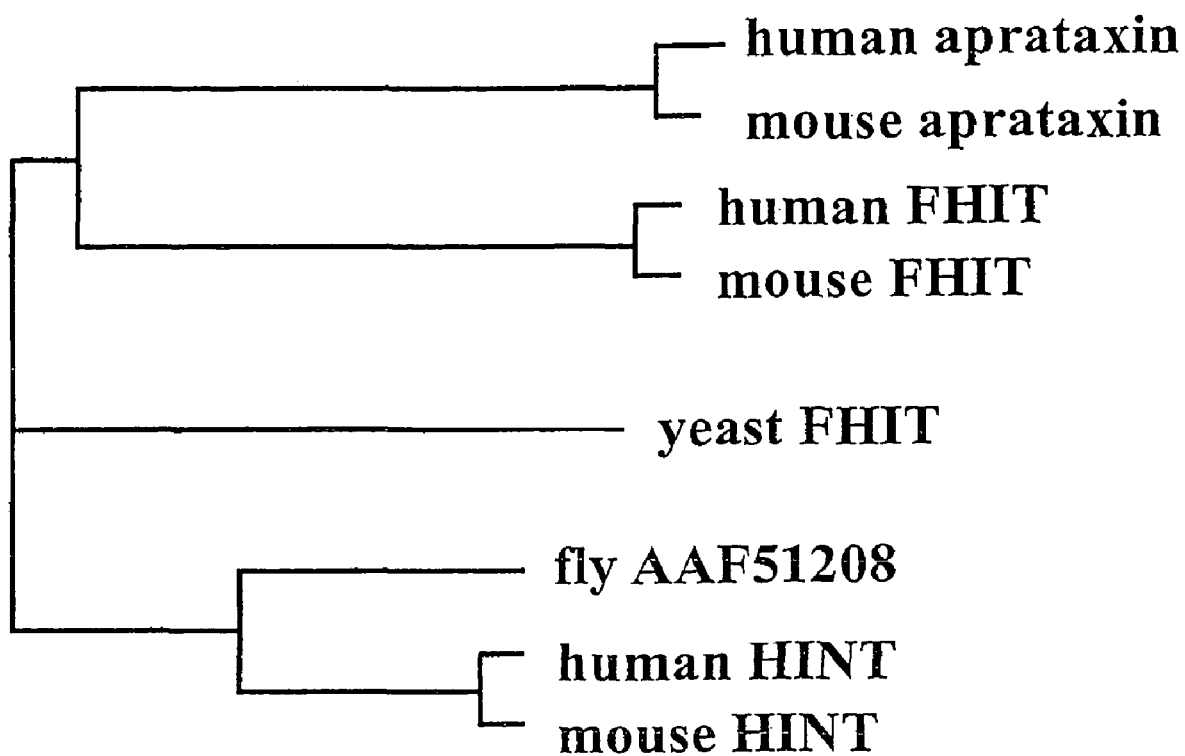
FIG. 4b shows phylogenetic trees of HIT superfamily proteins.

FIG. 4 shows multiple amino acid alignment, of ataxin with HIT superfamily proteins (FIG. 4a) and a phylogenic tree of HIT superfamily protein s (FIG. 4b). FIG. 4a shows CLUSTAL W alignment of the amino acid sequences of ataxin with HINT (histidine trial nucleotide-binding protein) and FHIT (fragile histidine triad protein) proteins. Duduced amino acid sequences of ataxin, mouse orthologue of ataxin, human HINT, mouse HINT, fly AAF51208, yeast HINT, human FHIT and mouse FHIT were aligned by CLUSTAL W, and conserved amino acid residues were shaded by GeneDoc (Thompson, J. D. et al., Nucleic Acids Res 22, 4673-80 (1994)). The darkness of the shade represents the strength of conservation (black, 100%; Dark gray, 80%; and Thin gray, 60%). Helical regions are denoted by closed gray arrow and β strands are denoted by black closed arrow according to the predicted secondary structure of HINT family protein (Lima, C. D. et al., Proc Natl Acd Sci USA 93, 5357-62 (1996)). The mutations were observed in the present study are shown above the alignment. Miss-sense mutations were observed at highly conserved amino acid residues among these HIT superfamily proteins.

FIG. 4b shows a phylogenetic tree of representative HIT superfamily proteins. The neighbor-joining distance tree was constructed based on alignments of amino acid sequence of HIT superfamily proteins shown in FIG. 5 (Saitou, N. et al., Mol Biol Evol 4, 406-25 (1987)).

Ataxin contains a highly conserved histidine triad (HIT) motif (His-φ-His-φ-His-φ-φ, where φ is a hydrophobic amino acid), an essential motif for HIT proteins (Brenner, C. et al., J Cell Physiol 181, 179-87 (1999); Seraphin, B. DNA Seq 3, 177-9 (1992)), and has a high homology to HIT proteins (FIG. 4a). HIT proteins have been classified into two branches: the Fhit (fragileHIT) protein family found only in animals and fungi, and the ancient histidine triad nucleotide-binding protein (HINT) family that has representatives in all cellular life (Brenner, C. et al., J Cell Physiol 181, 179-87 (1999); Seraphin, B. DNA Seq 3, 177-9 (1992)). These data and phylogenetic tree analysis demonstrated that ataxin is the third member of the HIT protein superfamily (FIGS. 4a,b).

Although nucleotide-binding and di-adenosine polyphosphate hydrolase activities have been implicated as the potential functions of HIT protein superfamily (Brenner, C. et al., J Cell Physiol 181, 179-87 (1999); Seraphin, B. DNA Seq 3, 177-9 (1992)) we firstly identify a distinct phenotype that is linked to mutations in the HIT protein superfamily. The P32L mutation involves the proline residue which is highly conserved among all the superfamilies (FIG. 4). The V89G mutation involves one of the hydrophobic amino acid of the histidine triad, which is also highly conserved among the HIT protein superfamily (FIG. 4). Since the HIT motif forms part of the phosphate-binding loop, the V89G mutation likely affects the phosphate-binding activity of the HIT motif.

INDUSTRIAL APPLICABILITY

As shown by the examples, the mutations of ataxin gene are proved to cause EAOH. The analysis of ataxin gene enables the confirmed diagnosis of EAOH. Since the genotype is correlated with the phenotype, it is possible to evaluate clinical features and prognosis based on gene diagnosis. Further, since the frameshift mutation and missense mutation caused by mutations of ataxin gene inhibit ataxin protein expression, ataxin gene and ataxin protein can be used for treating EAOH. Furthermore, the identification of ataxin gene as a causative gene of EAOH is a key to know a physiological functions of HIT protein superfamily as well as ataxin.

The present application claims priority to JP 2001-279719 filed on Sep. 14, 2001, the contents of which are incorporated herein by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for determining the presence of, or predisposition to early-onset spinocerebellar ataxia with ocular motor aprataxia and hypoalbuminemia in a human, comprising:

a) contacting polynucleotides isolated from a biological sample obtained from the human with a polynucleotide probe which comprises all, or a portion of, the nucleotide sequence of SEQ ID NO:1 or SEQ ID NO:3 and wherein the polynucleotide probe comprises at least one mutation: a Cytosine to Thymidine substitution at nucleotide 95 in SEQ ID NO:1; an insertion of a Thymidine between nucleotides 167 and 168 of SEQ ID NO:1; a Thymidine to Guanine substitution at nucleotide 266 in SEQ ID NO:1; a deletion of a Thymidine at nucleotide 318 in SEQ ID NO:1; a Cytosine to Thymidine substitution at nucleotide 617 in SEQ ID NO:3; an insertion of a Thymidine between nucleotides 689 and 690 of SEQ ID NO:3; a Thymidine to Guanine substitution at nucleotide 788 in SEQ ID NO:3; or a deletion of a Thymidine at nucleotide 840 in SEQ ID NO:3; and b) assessing whether specific hybridization has occurred between the polynucleotides in the sample and the polynucleotide probe, wherein if specific hybridization has occurred between the polynucleotide probe and the sample polynucleotide, the human has or is predisposed to early-onset spinocerebellar ataxia with ocular motor aprataxia and hypoalbuminemia.

2. A method of claim 1 wherein a combination of two mutations are detected.

3. A method of detecting a mutation in an aprataxin gene in a biological sample, comprising:

a) analyzing the nucleotide sequence of polynucleotides isolated from the biological sample to determine the nucleotide sequence of the aprataxin gene in the sample, and b) comparing the results of the nucleotide sequence analysis of the aprataxin gene in the sample of a) with the results of nucleotide sequence analysis of a control nucleotide sequence of the aprataxin gene wherein the control gene comprises the nucleotide sequence SEQ ID NO:1or SEQ ID NO:3 to determine differences between the aprataxin gene nucleotide sequence of the sample and the control aprataxin gene sequence;

wherein a difference between the nucleotide sequence of the sample aprataxin gene and the nucleotide sequence of the control aprataxin gene is indicative of a mutation in the sample aprataxin gene.

4. A method for determining the presence of, or predisposition to early-onset spinocerebellar ataxia with ocular motor aprataxia and hypoalbuminemia in a human, comprising:

a) amplifying polynucleotides isolated from a biological sample obtained from the human with primers that comprise all, or a portion of SEQ ID NO:1 or SEQ ID NO:3 and wherein the primers specifically amplify all, or a portion of SEQ ID NO: 1or SEQ ID NO. 3 that have at least one mutation is selected from the group consisting of:

an insertion of a Thymidine between nucleotides 167 and 168 of SEQ ID NO: 1;

a substitution of Cytosine to Thymidine at nucleotide 95 of SEQ ID NO:1;

a substitution of Thymidine to Guanine at nucleotide 266 of SEQ ID NO:1;

an insertion of a Thymidine between nucleotides 167 and 168 and a deletion of Thymidine at nucleotide 318 of SEQ ID NO:1;

an insertion of a Thymidine between nucleotides 689 and 690 and a substitution of Cytosine to Thymidine at nucleotide 617 of SEQ ID NO:3;

a substitution of Cytosine to Thymidine at nucleotide 617 and a substitution of Thymidine to Guanine at nucleotide 788 of SEQ ID NO: 3; and an insertion of a Thymidine between nucleotide 689 and 690 and a deletion of a Thymidine at nucleotide 840 of SEQ ID NO:3; and b) assessing the amplification of the polynucleotides and determining the presence or absence of a mutation in the amplified polynucleotides, wherein the presence of the mutation in the amplified polynucleotides indicates that the human has or is predisposed to early-onset spinocerebellar ataxia with ocular motor aparataxia and hypoalbuminemia.

5. The method of claim 4, wherein a combination of two mutations are detected.

6. A method for determining the presence of, or predisposition to early-onset spinocerebellar ataxia with ocular motor aprataxia and hypoalbuminemia in a human, comprising:
a) contacting polynucleotides isolated from a biological sample obtained from the human with all, or a portion of a polynucleotide probe which encodes a protein comprising the amino acid sequence of SEQ ID NO:2 or SEQ ID NO:4, and wherein the nucleotide sequence of the probe comprises at least one mutation selected from; a Cytosine to Thymidine substitution at nucleotide 95 in SEQ ID NO:1: an insertion of a Thymidine between nucleotides 167 and 168 of SEQ ID NO:1; a Thymidine to Guanine substitution at nucleotide 266 in SEQ ID NO:1; a deletion of a Thymidine at nucleotide 318 in SEQ ID NO:1; a Cytosine to Thymidine substitution at nucleotide 617 in SEQ ID NO:3; an insertion of a Thymidine between nucleotides 689 and 690 of SEQ ID NO:3; a Thymidine to Guanine substitution at nucleotide 788 in SEQ ID NO:3; and a deletion of a Thymidine at nucleotide 840 in SEQ ID NO:3; and
b) assessing whether specific hybridization has occurred between the polynucleotide in the sample and the polynucleotide probe, wherein if specific hybridization has occurred, the human has or is predisposed to early-onset spinocerebellar ataxia with ocular motor apraxia and hypoalbuminemia.

7. A method of claim 6, wherein
a combination of two mutations are detected.

8. A method of detecting the presence of or predisposition to early-onset spinocerebellar ataxia with ocular motor apratxia and hypoalbuminemia in a human comprising:
a) isolating a nucleic acid sample from said human that contains a nucleotide sequence of an aprataxin gene; and b) analyzing the nucleotide sequence of the aprataxin gene in the sample obtained from the human for a substitution mutation that results in a substitution of proline for leucine at amino acid 32, or a substitution of valine for glycine at amino acid 89 of SEQ ID NO:2; or a substitution of praline for leucine at amino acid 260, or a substitution of valine for glycine at amino acid 263 of SEQ ID NO:4;

wherein the presence of one or more substitution mutations in the aprataxin gene in the sample is indicative of the presence of, or predisposition to, early-onset spinocerebellar ataxia with ocular motor aprataxia and hypoalbuminemia in the human.

9. The method of claim 8, wherein the nucleic acid sample obtained from the human is amplified prior to analysis.

10. A method of detecting the presence of or predisposition to early-onset spinocerebellar ataxia with ocular motor apraxia and hypoalbuminemia in a human comprising:
a) isolating a nucleic acid sample from said human that contains a nucleotide sequence an aparataxin gene; and
b) analyzing the nucleotide sequence of the aparataxin gene in the sample obtained from the human for one or more mutations in the aprataxin gene that results in an insertion of a Thymidine between nucleotides 167 and 168 of SEQ ID NO: 1; and a substitution of Cytosine to Thymidine at nucleotide 95 of SEQ ID NO:1; a substitution of Cytosine to Thymidine at nucleotide 95 of SEQ ID NO:1 and a substitution of Thymidine to Guanine at nucleotide 266 of SEQ ID NO:1; an insertion of a Thymidine between nucleotides 167 and 168 and a deletion of Thymidine at nucleotide 318 of SEQ ID NO:1; an insertion of a Thymidine between nucleotides 689 and 690 and a substitution of Cytosine to Thymidine at nucleotide 617 of SEQ ID NO:3; a substitution of Cytosine to Thymidine at nucleotide 617 and a substitution of Thymidine to Guanine at nucleotide 788 of SEQ ID NO: 3; or an insertion of a Thymidine between nucleotide 689 and 690 and a deletion of a Thymidine at nucleotide 840 of SEQ ID NO:3,
wherein the presence of one or more mutations in the aprataxin gene in the sample is indicative of the presence of or predisposition to, early-onset spinocerebellar ataxia with ocular motor aprataxia and hypoalbuminemia in the human.

11. The method of claim 10, wherein the nucleic acid sample obtained from the human is amplified prior to analysis.

12. The method of claim 8, wherein the nucleotide sequence analysis is by direct sequencing of the nucleic acids in the sample.

13. The method of claim 10, wherein the nucleotide sequence analysis is by direct sequencing of the nucleic acids in the sample.

* * * * *

UNITED STATES PATENT AND TRADEMARK OFFICE
CERTIFICATE OF CORRECTION

| | | |
|---|---|---|
| PATENT NO. | : 7,824,860 B2 | Page 1 of 1 |
| APPLICATION NO. | : 11/496284 | |
| DATED | : November 2, 2010 | |
| INVENTOR(S) | : Shoji Tsuji | |

It is certified that error appears in the above-identified patent and that said Letters Patent is hereby corrected as shown below:

Column 38, Claim 8, line 6, delete "praline" and insert -- proline --.

Signed and Sealed this
Eleventh Day of January, 2011

David J. Kappos
*Director of the United States Patent and Trademark Office*

SEQUENCE LISTING

<160> NUMBER OF SEQ ID NOS: 24

<210> SEQ ID NO 1

<211> LENGTH: 1408
<212> TYPE: DNA
<213> ORGANISM: Homo sapiens
<220> FEATURE:
<221> NAME/KEY: CDS
<222> LOCATION: (1)..(507)
<223> OTHER INFORMATION:
<220> FEATURE:
<221> NAME/KEY: misc_feature
<222> LOCATION: (10)..(270)
<223> OTHER INFORMATION: HIT region

<400> SEQUENCE: 1

| | | | | | | | | | | | | | | | | |
|---|---|---|---|---|---|---|---|---|---|---|---|---|---|---|---|---|
| atg | cag | gac | ccc | aaa | atg | cag | gtt | tac | aaa | gat | gag | cag | gtg | gtg | gtg | 48 |
| Met | Gln | Asp | Pro | Lys | Met | Gln | Val | Tyr | Lys | Asp | Glu | Gln | Val | Val | Val | |
| 1 | | | | 5 | | | | | 10 | | | | | 15 | | |
| ata | aag | gat | aaa | tac | cca | aag | gcc | cgt | tac | cat | tgg | ctg | gtc | tta | ccg | 96 |
| Ile | Lys | Asp | Lys | Tyr | Pro | Lys | Ala | Arg | Tyr | His | Trp | Leu | Val | Leu | Pro | |
| | | | 20 | | | | | 25 | | | | | 30 | | | |
| tgg | acc | tcc | att | tcc | agt | ctg | aag | gct | gtg | gcc | agg | gaa | cac | ctt | gaa | 144 |
| Trp | Thr | Ser | Ile | Ser | Ser | Leu | Lys | Ala | Val | Ala | Arg | Glu | His | Leu | Glu | |
| | 35 | | | | | 40 | | | | | 45 | | | | | |
| ctc | ctt | aag | cat | atg | cac | act | gtg | ggg | gaa | aag | gtg | att | gta | gat | ttt | 192 |
| Leu | Leu | Lys | His | Met | His | Thr | Val | Gly | Glu | Lys | Val | Ile | Val | Asp | Phe | |
| 50 | | | | | 55 | | | | | 60 | | | | | | |
| gct | ggg | tcc | agc | aaa | ctc | cgc | ttc | cga | ttg | ggc | tac | cac | gcc | att | ccg | 240 |
| Ala | Gly | Ser | Ser | Lys | Leu | Arg | Phe | Arg | Leu | Gly | Tyr | His | Ala | Ile | Pro | |
| 65 | | | | | 70 | | | | | 75 | | | | | 80 | |
| agt | atg | agc | cat | gta | cat | ctt | cat | gtg | atc | agc | cag | gat | ttt | gat | tct | 288 |
| Ser | Met | Ser | His | Val | His | Leu | His | Val | Ile | Ser | Gln | Asp | Phe | Asp | Ser | |
| | | | | 85 | | | | | 90 | | | | | 95 | | |
| cct | tgc | ctt | aaa | aac | aaa | aaa | cat | tgg | aat | tct | ttc | aat | aca | gaa | tac | 336 |
| Pro | Cys | Leu | Lys | Asn | Lys | Lys | His | Trp | Asn | Ser | Phe | Asn | Thr | Glu | Tyr | |
| | | | 100 | | | | | 105 | | | | | 110 | | | |
| ttc | cta | gaa | tca | caa | gct | gtg | atc | gag | atg | gta | caa | gag | gct | ggt | aga | 384 |
| Phe | Leu | Glu | Ser | Gln | Ala | Val | Ile | Glu | Met | Val | Gln | Glu | Ala | Gly | Arg | |
| | 115 | | | | | 120 | | | | | 125 | | | | | |
| gta | act | gtc | cga | gat | ggg | atg | cct | gag | ctc | ttg | aag | ctg | ccc | ctt | cgt | 432 |
| Val | Thr | Val | Arg | Asp | Gly | Met | Pro | Glu | Leu | Leu | Lys | Leu | Pro | Leu | Arg | |
| 130 | | | | | 135 | | | | | 140 | | | | | | |
| tgt | cat | gag | tgc | cag | cag | ctg | ctg | cct | tcc | att | cct | cag | ctg | aaa | gaa | 480 |
| Cys | His | Glu | Cys | Gln | Gln | Leu | Leu | Pro | Ser | Ile | Pro | Gln | Leu | Lys | Glu | |
| 145 | | | | | 150 | | | | | 155 | | | | | 160 | |
| cat | ctc | agg | aag | cac | tgg | aca | cag | tga | ttctgcagag | | | cctgagctgc | | | | 527 |
| His | Leu | Arg | Lys | His | Trp | Thr | Gln | | | | | | | | | |
| | | | | 165 | | | | | | | | | | | | | tgctgtggtg tggcccactg gagcaaactg ctggcaccta ttctggttg cttgtgaact 587
tctactcatt tcctaaatta aaacatgcag ctttttcaca aatttattct attattgagt 647
ggccacaatg tagagtggct caaagtactt caggattagg aatttgggtt tgtcatagat 707
gtattctctg gtgagggtgg ctgggatata cctgacccac catcttcaga aggacccatg 767
tcaggtctga ccattgggag caaagccatg ttcacactga cctaatgcag agtatggaag 827
cattgggctg gttatacatt tctgtttctt agatttatcc tccgcctctg taggcatgga 887
caacctttaa tcagagcatc tagagtggcc tcttgtttat cctgaaggta ctgatgggtc 947
ttgttttctg ttagtctgtt ttgtaatatt cttttcccct ccttcatggg gaggcttagt 1007
ttgtccagtc cttccatgcc cttctatccc agattaccta aatgttccct tctcaggaat 1067
tctgtactca tcagttcttc acagtgagaa aagaggctag atgatggtgt gggggggttgg 1127
agttttcttc taataccgag ggttcctggc tgtgaggaaa cagccacatg ttcgtcatga 1187

```
ttgagctgtg aagtcttctt ggacctgttg tctgaaaata agttaattt gtttgaggca      1247 tctctcttaa gtaggtggaa actattgaag ttcagctaac aatcacagca taggttctga      1307
tgcatggaaa ggtggttggt gaatgaaaaa gttgcgtaga gccactactt tctttttccc      1367
tgagaataaa tttggataaa aaaaaaaaaa aaaaaaaaa a                           1408
```

<210> SEQ ID NO 2
<211> LENGTH: 168
<212> TYPE: PRT
<213> ORGANISM: Homo sapiens
<220> FEATURE:
<221> NAME/KEY: misc_feature
<222> LOCATION: (10)..(270)
<223> OTHER INFORMATION: HIT region

<400> SEQUENCE: 2

```
Met Gln Asp Pro Lys Met Gln Val Tyr Lys Asp Glu Gln Val Val
1               5                   10                  15

Ile Lys Asp Lys Tyr Pro Lys Ala Arg Tyr His Trp Leu Val Leu Pro
            20                  25                  30

Trp Thr Ser Ile Ser Ser Leu Lys Ala Val Ala Arg Glu His Leu Glu
        35                  40                  45

Leu Leu Lys His Met His Thr Val Gly Glu Lys Val Ile Val Asp Phe
50                  55                  60

Ala Gly Ser Ser Lys Leu Arg Phe Arg Leu Gly Tyr His Ala Ile Pro
65                  70                  75                  80

Ser Met Ser His Val His Leu His Val Ile Ser Gln Asp Phe Asp Ser
                85                  90                  95

Pro Cys Leu Lys Asn Lys Lys His Trp Asn Ser Phe Asn Thr Glu Tyr
            100                 105                 110

Phe Leu Glu Ser Gln Ala Val Ile Glu Met Val Gln Glu Ala Gly Arg
        115                 120                 125

Val Thr Val Arg Asp Gly Met Pro Glu Leu Leu Lys Leu Pro Leu Arg
    130                 135                 140

Cys His Glu Cys Gln Gln Leu Leu Pro Ser Ile Pro Gln Leu Lys Glu
145                 150                 155                 160

His Leu Arg Lys His Trp Thr Gln
                165
```

<210> SEQ ID NO 3
<211> LENGTH: 1187
<212> TYPE: DNA
<213> ORGANISM: Homo sapiens
<220> FEATURE:
<221> NAME/KEY: CDS
<222> LOCATION: (7)..(1032)
<223> OTHER INFORMATION:

<400> SEQUENCE: 3

```
agagtg atg atg cgg gtg tgc tgg ttg gtg aga cag gac agc cgg cac        48
       Met Met Arg Val Cys Trp Leu Val Arg Gln Asp Ser Arg His
       1               5                   10 cag cga atc aga ctt cca cat ttg gaa gca gtt gtg att ggg cgt ggc       96
Gln Arg Ile Arg Leu Pro His Leu Glu Ala Val Val Ile Gly Arg Gly
15                  20                  25                  30 cca gag acc aag atc act gat aag aaa tgt tct cga cag caa gta cag      144
Pro Glu Thr Lys Ile Thr Asp Lys Lys Cys Ser Arg Gln Gln Val Gln
                35                  40                  45 ttg aaa gca gag tgt aac aag gga tat gtc aag gta aag cag gta gga      192
Leu Lys Ala Glu Cys Asn Lys Gly Tyr Val Lys Val Lys Gln Val Gly
```

```
                Leu Lys Ala Glu Cys Asn Lys Gly Tyr Val Lys Val Lys Gln Val Gly
                         50                  55                  60 gtc aat ccc acc agc att gac tca gtc gta att ggg aag gac caa gag       240
Val Asn Pro Thr Ser Ile Asp Ser Val Val Ile Gly Lys Asp Gln Glu
             65                  70                  75 gtg aag ctg cag cct ggc cag gtt ctc cac atg gtg aat gaa ctt tat       288
Val Lys Leu Gln Pro Gly Gln Val Leu His Met Val Asn Glu Leu Tyr
         80                  85                  90 cca tat att gta gag ttt gag gaa gag gca aag aac cct ggc ctg gaa       336
Pro Tyr Ile Val Glu Phe Glu Glu Glu Ala Lys Asn Pro Gly Leu Glu
 95                 100                 105                 110 aca cac agg aag aga aag aga tca ggc aac agt gat tct ata gaa agg       384
Thr His Arg Lys Arg Lys Arg Ser Gly Asn Ser Asp Ser Ile Glu Arg
                115                 120                 125 gat gct gct cag gaa gct gag gct ggg aca ggg ctg gaa cct ggg agc       432
Asp Ala Ala Gln Glu Ala Glu Ala Gly Thr Gly Leu Glu Pro Gly Ser
            130                 135                 140 aac tct ggc caa tgc tct gtg ccc cta aag aag gga aaa gat gca cct       480
Asn Ser Gly Gln Cys Ser Val Pro Leu Lys Lys Gly Lys Asp Ala Pro
        145                 150                 155 atc aaa aag gaa tcc ctg ggc cac tgg agt caa ggc ttg aag att tct       528
Ile Lys Lys Glu Ser Leu Gly His Trp Ser Gln Gly Leu Lys Ile Ser
    160                 165                 170 atg cag gac ccc aaa atg cag gtt tac aaa gat gag cag gtg gtg gtg       576
Met Gln Asp Pro Lys Met Gln Val Tyr Lys Asp Glu Gln Val Val Val
175                 180                 185                 190 ata aag gat aaa tac cca aag gcc cgt tac cat tgg ctg gtc tta ccg       624
Ile Lys Asp Lys Tyr Pro Lys Ala Arg Tyr His Trp Leu Val Leu Pro
                195                 200                 205 tgg acc tcc att tcc agt ctg aag gct gtg gcc agg gaa cac ctt gaa       672
Trp Thr Ser Ile Ser Ser Leu Lys Ala Val Ala Arg Glu His Leu Glu
            210                 215                 220 ctc ctt aag cat atg cac act gtg ggg gaa aag gtg att gta gat ttt       720
Leu Leu Lys His Met His Thr Val Gly Glu Lys Val Ile Val Asp Phe
        225                 230                 235 gct ggg tcc agc aaa ctc cgc ttc cga ttg ggc tac cac gcc att ccg       768
Ala Gly Ser Ser Lys Leu Arg Phe Arg Leu Gly Tyr His Ala Ile Pro
    240                 245                 250 agt atg agc cat gta cat ctt cat gtg atc agc cag gat ttt gat tct       816
Ser Met Ser His Val His Leu His Val Ile Ser Gln Asp Phe Asp Ser
255                 260                 265                 270 cct tgc ctt aaa aac aaa aaa cat tgg aat tct ttc aat aca gaa tac       864
Pro Cys Leu Lys Asn Lys Lys His Trp Asn Ser Phe Asn Thr Glu Tyr
                275                 280                 285 ttc cta gaa tca caa gct gtg atc gag atg gta caa gag gct ggt aga       912
Phe Leu Glu Ser Gln Ala Val Ile Glu Met Val Gln Glu Ala Gly Arg
            290                 295                 300 gta act gtc cga gat ggg atg cct gag ctc ttg aag ctg ccc ctt cgt       960
Val Thr Val Arg Asp Gly Met Pro Glu Leu Leu Lys Leu Pro Leu Arg
        305                 310                 315 tgt cat gag tgc cag cag ctg ctg cct tcc att cct cag ctg aaa gaa      1008
Cys His Glu Cys Gln Gln Leu Leu Pro Ser Ile Pro Gln Leu Lys Glu
    320                 325                 330 cat ctc agg aag cac tgg aca cag tgattctgca gagcctgagc tgctgctgtg     1062
His Leu Arg Lys His Trp Thr Gln
335                 340 gtgtggccca ctggagcaaa ctgctggcac ctattctggg ttgcttgtga acttctactc   1122
atttcctaaa ttaaacatg cagcttttc acaaaaaaaa aaaaaaaaa aaaaaaaaa       1182
``` aaaaa                                                                    1187

<210> SEQ ID NO 4
<211> LENGTH: 342
<212> TYPE: PRT
<213> ORGANISM: Homo sapiens

<400> SEQUENCE: 4

```
Met Met Arg Val Cys Trp Leu Val Arg Gln Asp Ser Arg His Gln Arg
1               5                   10                  15

Ile Arg Leu Pro His Leu Glu Ala Val Val Ile Gly Arg Gly Pro Glu
            20                  25                  30

Thr Lys Ile Thr Asp Lys Lys Cys Ser Arg Gln Gln Val Gln Leu Lys
        35                  40                  45

Ala Glu Cys Asn Lys Gly Tyr Val Lys Val Lys Gln Val Gly Val Asn
    50                  55                  60

Pro Thr Ser Ile Asp Ser Val Val Ile Gly Lys Asp Gln Glu Val Lys
65                  70                  75                  80

Leu Gln Pro Gly Gln Val Leu His Met Val Asn Glu Leu Tyr Pro Tyr
                85                  90                  95

Ile Val Glu Phe Glu Glu Ala Lys Asn Pro Gly Leu Glu Thr His
            100                 105                 110

Arg Lys Arg Lys Arg Ser Gly Asn Ser Asp Ser Ile Glu Arg Asp Ala
        115                 120                 125

Ala Gln Glu Ala Glu Ala Gly Thr Gly Leu Glu Pro Gly Ser Asn Ser
    130                 135                 140

Gly Gln Cys Ser Val Pro Leu Lys Lys Gly Lys Asp Ala Pro Ile Lys
145                 150                 155                 160

Lys Glu Ser Leu Gly His Trp Ser Gln Gly Leu Lys Ile Ser Met Gln
                165                 170                 175

Asp Pro Lys Met Gln Val Tyr Lys Asp Glu Gln Val Val Val Ile Lys
            180                 185                 190

Asp Lys Tyr Pro Lys Ala Arg Tyr His Trp Leu Val Leu Pro Trp Thr
        195                 200                 205

Ser Ile Ser Ser Leu Lys Ala Val Ala Arg Glu His Leu Glu Leu Leu
    210                 215                 220

Lys His Met His His Thr Val Gly Glu Lys Val Ile Val Asp Phe Ala Gly
225                 230                 235                 240

Ser Ser Lys Leu Arg Phe Arg Leu Gly Tyr His Ala Ile Pro Ser Met
                245                 250                 255

Ser His Val His Leu His Val Ile Ser Gln Asp Phe Asp Ser Pro Cys
            260                 265                 270

Leu Lys Asn Lys Lys His Trp Asn Ser Phe Asn Thr Glu Tyr Phe Leu
        275                 280                 285

Glu Ser Gln Ala Val Ile Glu Met Val Gln Ala Gly Arg Val Thr
    290                 295                 300

Val Arg Asp Gly Met Pro Glu Leu Leu Lys Leu Pro Leu Arg Cys His
305                 310                 315                 320

Glu Cys Gln Gln Leu Leu Pro Ser Ile Pro Gln Leu Lys Glu His Leu
                325                 330                 335

Arg Lys His Trp Thr Gln
            340
```

<210> SEQ ID NO 5
<211> LENGTH: 20

```
<212> TYPE: DNA
<213> ORGANISM: Artificial Sequence
<220> FEATURE:
<223> OTHER INFORMATION: synthetic DNA

<400> SEQUENCE: 5
atgtggagaa attggaggca                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic DNA

<400> SEQUENCE: 6
tgtgaaggaa ttgagctggt                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic DNA

<400> SEQUENCE: 7
ttggttttga tgtgcttcca                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic DNA

<400> SEQUENCE: 8
gaagcaggta gaagaggagt                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic DNA

<400> SEQUENCE: 9
ttcacaagca acccagaata                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic DNA

<400> SEQUENCE: 10
ccgtgagaat tagtggagtt                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic DNA

<400> SEQUENCE: 11
```

-continued gtgaaaacca aggaacactg                                                                                    20

<210> SEQ ID NO 12
<211> LENGTH: 20
<212> TYPE: DNA
<213> ORGANISM: Artificial Sequence
<220> FEATURE:
<223> OTHER INFORMATION: synthetic DNA

<400> SEQUENCE: 12
cagaggcttt tcccattttg                                                                                    20

<210> SEQ ID NO 13
<211> LENGTH: 20
<212> TYPE: DNA
<213> ORGANISM: Artificial Sequence
<220> FEATURE:
<223> OTHER INFORMATION: synthetic DNA

<400> SEQUENCE: 13
gggtctcagt gcaatatgtg                                                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic DNA

<400> SEQUENCE: 14
atttcagtgc tctcctctct                                                                                    20

<210> SEQ ID NO 15
<211> LENGTH: 20
<212> TYPE: DNA
<213> ORGANISM: Artificial Sequence
<220> FEATURE:
<223> OTHER INFORMATION: synthetic DNA

<400> SEQUENCE: 15
tctgtggagt ggtcatttac                                                                                    20

<210> SEQ ID NO 16
<211> LENGTH: 20
<212> TYPE: DNA
<213> ORGANISM: Artificial Sequence
<220> FEATURE:
<223> OTHER INFORMATION: synthetic DNA

<400> SEQUENCE: 16
tataggaagg caatggagtg                                                                                    20

<210> SEQ ID NO 17
<211> LENGTH: 168
<212> TYPE: PRT
<213> ORGANISM: Homo sapiens

<400> SEQUENCE: 17

Met Gln Asp Pro Lys Met Gln Val Tyr Lys Asp Glu Gln Val Val
1               5                   10                  15

Ile Lys Asp Lys Tyr Pro Lys Ala Arg Tyr His Trp Leu Val Leu Pro
                20                  25                  30

Trp Thr Ser Ile Ser Ser Leu Lys Ala Val Ala Arg Glu His Leu Glu
        35                  40                  45

```
Leu Leu Lys His Met His Thr Val Gly Glu Lys Val Ile Val Asp Phe
    50                  55                  60

Ala Gly Ser Ser Lys Leu Arg Phe Arg Leu Gly Tyr His Ala Ile Pro
 65                  70                  75                  80

Ser Met Ser His Val His Leu His Val Ile Ser Gln Asp Phe Asp Ser
                 85                  90                  95

Pro Cys Leu Lys Asn Lys Lys His Trp Asn Ser Phe Asn Thr Glu Tyr
            100                 105                 110

Phe Leu Glu Ser Gln Ala Val Ile Glu Met Val Gln Glu Ala Gly Arg
        115                 120                 125

Val Thr Val Arg Asp Gly Met Pro Glu Leu Leu Lys Leu Pro Leu Arg
    130                 135                 140

Cys His Glu Cys Gln Gln Leu Leu Pro Ser Ile Pro Gln Leu Lys Glu
145                 150                 155                 160

His Leu Arg Lys His Trp Thr Gln
                165
```

<210> SEQ ID NO 18
<211> LENGTH: 166
<212> TYPE: PRT
<213> ORGANISM: Mus sp.

<400> SEQUENCE: 18

```
Met Lys Asp Pro Lys Met Gln Val Tyr Lys Asp Asp Gln Val Val Val
 1               5                  10                  15

Ile Lys Asp Lys Tyr Pro Lys Ala Arg His Trp Leu Val Leu Pro Trp
            20                  25                  30

Ala Ser Ile Ser Ser Leu Lys Val Val Thr Ser Glu His Leu Glu Leu
        35                  40                  45

Leu Lys His Met His Thr Val Gly Glu Lys Val Ile Val Asp Phe Ala
    50                  55                  60

Gly Ser Ser Lys Arg Phe Arg Leu Gly Tyr His Ala Ile Pro Ser Met
 65                  70                  75                  80

Ser His Val His Leu His Val Ile Ser Gln Asp Phe Asp Ser Pro Cys
                 85                  90                  95

Leu Lys Asn Lys Lys His Trp Asn Ser Phe Asn Thr Glu Tyr Pro Leu
            100                 105                 110

Glu Ser Gln Ala Val Ile Lys Met Val Gln Glu Ala Gly Arg Val Thr
        115                 120                 125

Val Lys Asp Gly Thr Cys Glu Leu Leu Lys Leu Pro Leu Arg Cys His
    130                 135                 140

Glu Cys Gln Gln Leu Leu Pro Ser Ile Pro Gln Leu Lys Glu His Leu
145                 150                 155                 160

Arg Lys His Trp Gly Gly
                165
```

<210> SEQ ID NO 19
<211> LENGTH: 126
<212> TYPE: PRT
<213> ORGANISM: Homo sapiens

<400> SEQUENCE: 19

```
Met Ala Asp Glu Ile Ala Lys Ala Gln Val Ala Arg Pro Gly Gly Asp
 1               5                  10                  15

Thr Ile Phe Gly Lys Ile Ile Arg Lys Glu Arg Pro Ala Lys Ile Ile
            20                  25                  30
```

```
Phe Glu Asp Asp Arg Cys Leu Ala Phe His Asp Ile Ser Pro Gln Ala
            35                  40                  45

Pro Thr His Phe Leu Val Ile Pro Lys Lys His Ile Ser Gln Leu Ser
        50                  55                  60

Val Ala Glu Asp Asp Glu Ser Leu Leu Gly His Leu Met Ile Val
65                  70                  75                  80

Gly Lys Lys Cys Ala Ala Asp Leu Gly Leu Asn Lys Gly Tyr Arg Met
                85                  90                  95

Val Val Asn Glu Gly Ser Asp Gly Gln Ser Val Tyr His Val His
                100                 105                 110

Leu His Val Leu Gly Gly Arg Gln Met His Trp Pro Pro Gly
            115                 120                 125

<210> SEQ ID NO 20
<211> LENGTH: 126
<212> TYPE: PRT
<213> ORGANISM: Mus sp.

<400> SEQUENCE: 20

Met Ala Asp Glu Ile Ala Lys Ala Gln Val Ala Arg Pro Gly Gly Asp
1               5                   10                  15

Thr Ile Phe Gly Lys Ile Ile Arg Lys Glu Arg Pro Ala Lys Ile Ile
            20                  25                  30

Phe Glu Asp Asp Arg Cys Leu Ala Phe His Asp Ile Ser Pro Gln Ala
            35                  40                  45

Pro Thr His Phe Leu Val Ile Pro Lys Lys His Ile Ser Gln Leu Ser
        50                  55                  60

Val Ala Glu Asp Asp Glu Ser Leu Leu Gly His Leu Met Ile Val
65                  70                  75                  80

Gly Lys Lys Cys Ala Ala Asp Leu Gly Leu Lys Arg Gly Tyr Arg Met
                85                  90                  95

Val Val Asn Glu Gly Ser Asp Gly Gly Gln Ser Val Tyr His Val His
                100                 105                 110

Leu His Val Leu Gly Gly Arg Gln Met Asn Trp Pro Pro Gly
            115                 120                 125

<210> SEQ ID NO 21
<211> LENGTH: 126
<212> TYPE: PRT
<213> ORGANISM: Drosophila sp.

<400> SEQUENCE: 21

Met Ala Ser Glu Val Glu Lys Ser Gln Thr Ala Ala Ser Glu Asp
1               5                   10                  15

Thr Ile Phe Gly Lys Ile Leu Arg Lys Glu Ile Pro Cys Lys Phe Ile
            20                  25                  30

His Glu Asp Asp Lys Cys Val Ala Phe His Asp Val Ala Pro Gln Ala
            35                  40                  45

Pro Thr His Phe Leu Val Ile Pro Arg Lys Pro Ile Ala Gln Leu Ser
        50                  55                  60

Leu Ala Glu Asp Gly Asp Ala Asp Leu Leu Gly His Leu Met Leu Val
65                  70                  75                  80

Gly Arg Lys Val Ala Lys Glu Leu Gly Leu Ala Asp Gly Tyr Arg Val
                85                  90                  95

Val Ile Asn Asn Gly Lys His Gly Ala Gln Ser Val Tyr His Leu His
                100                 105                 110
```

```
Leu His Phe Leu Gly Gly Arg Gln Met Gln Trp Pro Pro Gly
        115                 120                 125

<210> SEQ ID NO 22
<211> LENGTH: 138
<212> TYPE: PRT
<213> ORGANISM: Saccharomyces sp.

<400> SEQUENCE: 22

Met Glu Pro Leu Ile Ser Ala Pro Tyr Leu Thr Thr Thr Lys Met Ser
1               5                   10                  15

Ala Pro Ala Thr Leu Asp Ala Ala Cys Ile Phe Cys Lys Ile Ile Lys
            20                  25                  30

Ser Glu Ile Pro Ser Phe Lys Leu Ile Glu Thr Lys Tyr Ser Tyr Ala
        35                  40                  45

Phe Leu Asp Ile Gln Pro Thr Ala Glu Gly His Ala Leu Ile Ile Pro
    50                  55                  60

Lys Tyr His Gly Ala Lys Leu His Asp Ile Pro Asp Glu Phe Leu Thr
65                  70                  75                  80

Asp Ala Met Pro Ile Ala Lys Arg Leu Ala Lys Ala Met Lys Leu Asp
                85                  90                  95

Thr Tyr Asn Val Leu Gln Asn Asn Gly Lys Ile Ala His Gln Glu Val
            100                 105                 110

Asp His Val His Phe His Leu Ile Pro Lys Arg Asp Glu Lys Ser Gly
        115                 120                 125

Leu Ile Val Gly Trp Pro Ala Gln Glu Thr
    130                 135

<210> SEQ ID NO 23
<211> LENGTH: 147
<212> TYPE: PRT
<213> ORGANISM: Homo sapiens

<400> SEQUENCE: 23

Met Ser Phe Arg Phe Gly Gln His Leu Ile Lys Pro Ser Val Val Phe
1               5                   10                  15

Leu Lys Thr Glu Leu Ser Phe Ala Leu Val Asn Arg Lys Pro Val Val
            20                  25                  30

Pro Gly His Val Leu Val Cys Pro Leu Arg Pro Val Glu Arg Phe His
        35                  40                  45

Asp Leu Arg Pro Asp Glu Val Ala Asp Leu Phe Gln Thr Thr Gln Arg
    50                  55                  60

Val Gly Thr Val Val Glu Lys His Phe His Gly Thr Ser Leu Thr Phe
65                  70                  75                  80

Ser Met Gln Asp Gly Pro Glu Ala Gly Gln Thr Val Lys His Val His
                85                  90                  95

Val His Val Leu Pro Arg Lys Ala Gly Asp Phe His Arg Asn Asp Ser
            100                 105                 110

Ile Tyr Glu Glu Leu Gln Lys His Asp Lys Glu Asp Phe Pro Ala Ser
        115                 120                 125

Trp Arg Ser Glu Glu Glu Met Ala Ala Glu Ala Ala Ala Leu Arg Val
    130                 135                 140

Tyr Phe Gln
145

<210> SEQ ID NO 24
<211> LENGTH: 148
```

```
-continued

<212> TYPE: PRT
<213> ORGANISM: Mus sp.

<400> SEQUENCE: 24

Met Ser Phe Arg Phe Gly Gln His Leu Ile Lys Pro Ser Val Val Phe
1               5                   10                  15

Leu Lys Thr Glu Leu Ser Phe Ala Leu Val Asn Arg Lys Pro Val Val
            20                  25                  30

Pro Gly His Val Leu Val Cys Pro Leu Arg Pro Val Glu Arg Phe Arg
        35                  40                  45

Asp Leu His Pro Asp Glu Val Ala Asp Leu Phe Gln Val Thr Gln Arg
    50                  55                  60

Val Gly Thr Val Val Glu Lys His Phe Gln Gly Thr Ser Leu Thr Phe
65                  70                  75                  80

Ser Met Gln Asp Gly Pro Glu Ala Gly Gln Thr Val Lys His Val His
                85                  90                  95

Val His Val Leu Pro Arg Lys Ala Gly Asp Phe Pro Arg Asn Asp Asn
            100                 105                 110

Ile Tyr Asp Glu Leu Gln Lys His Asp Arg Glu Asp Ser Pro Ala Phe
        115                 120                 125

Trp Arg Ser Glu Lys Glu Met Ala Ala Glu Ala Glu Ala Leu Arg Val
    130                 135                 140

Tyr Phe Gln Ala
145
```